US005545617A

United States Patent [19]
Dartt et al.

[11] Patent Number: 5,545,617
[45] Date of Patent: Aug. 13, 1996

[54] THERAPEUTIC REGULATION OF ABNORMAL CONJUNCTIVAL GOBLET CELL MUCOUS SECRETION

[75] Inventors: Darlene A. Dartt, Newton; Timothy L. Kessler, Boston, both of Mass.

[73] Assignee: The Schepens Eye Research Institute, Inc., Boston, Mass.

[21] Appl. No.: 152,175

[22] Filed: Nov. 12, 1993

[51] Int. Cl.$^6$ .......................... A61K 38/16; A61K 49/00; C12Q 1/02; G01N 33/48
[52] U.S. Cl. .............................. 514/12; 514/21; 514/912; 514/914; 435/4; 435/29; 436/63
[58] Field of Search ................................. 424/2, 9; 435/4, 435/29; 436/63; 514/12, 21, 816, 817, 818, 912, 914, 915

[56] References Cited

U.S. PATENT DOCUMENTS

| | | | |
|---|---|---|---|
| 4,002,168 | 1/1977 | Petterson | 604/298 |
| 4,454,151 | 6/1984 | Waterbury | 514/413 |
| 4,540,408 | 9/1985 | Lloyd | 604/294 |
| 4,745,100 | 5/1988 | Gilbard et al. | 514/12 |
| 4,753,945 | 6/1988 | Gilbard et al. | 514/263 |
| 4,861,760 | 8/1989 | Mazuel et al. | 514/54 |
| 4,868,154 | 9/1989 | Gilbard et al. | 514/13 |
| 4,911,933 | 3/1990 | Gilbard | 424/663 |
| 4,956,348 | 9/1990 | Gilbard et al. | 514/47 |

OTHER PUBLICATIONS

Dartt et al., "Stimulation of Rat Conjunctival Goblet Cell Mucous Secretion,"Journal Cell of Biology 115:15a (1991).
Kessler et al., "Neural stimulaion of conjunctival goblet cell mucous secretion in rats," Abstract. Int'l Conf. on the Lacrimal Gland Tear Film and Dry Eye Syndrome: Basic Science and Clinical Relevance. Southampton Parish, Bermuda. Nov. 14–17, 1992.
Kessler et al., "Effect of adrenergic and agonists ckolinergicc and neural stimulation on goblet cell mucous secretion in rats," ARVO Abstract. Invest. Ophthalmol. Vis. Sci. 34:(Suppl):822 (1993).
Akhtar, "Effects of norepinephrine and 5–hydroxytryptamine on phosphoinositide–$PO_4$ turnover in rabbit cornea", Exp. Eye Res. 44:849–862 (1987).
Allansmith et al., "Density of goblet cells in vernal conjunctivitis and contact lens–associated giant papillary conjunctivitis", Arch. Ophthalmol. 9884–885 (1981).
Argona et al., "Effects of a stable analogue of $PGE_2$(11–deoxy-13,14–didehydro–16(s)–methylester methyl $PGE_2FCE$ 20700) on the secretory processes of conjunctival goblet cells of rabbit," Exp. Eye Res. 45:647–654 (1987).
Augeron et al., "Neurotensin and neuromedin N stimulate mucin output from human goblet cells (Cl. 16E) via neurotensin receptors," Am. J. Physiol. 262:G470–G476 (1992).
Barnes et al., "Inflammatory mediators and asthma", Pharm. Rev. 40:4984 (1988).
Basbaum et al., "The serous cell," Ann. Rev. Physiol. 52:97–144 (1990).
Braga et al., "Classification of agents that act on bronchial mucus" In: Drugs and Brochial Mucology; edited by PC Braga and L. Allegra, New York: Raven Press, pp. 59–67 (1989).
Butler et al., "Effects of VIIth (facial) nerve degeneration on vasoactive intestinal polypeptide and substance P levels in ocular and orbital tissues of the rabbit", Exp. Eye Res. 39:523–532 (1984).

(List continued on next page.)

Primary Examiner—Mindy Fleisher
Assistant Examiner—Nancy J. Degen
Attorney, Agent, or Firm—Weingarten, Schurgin, Gagnebin & Hayes

[57] ABSTRACT

A method of treating patients suffering from aberrant conjunctival goblet cell mucous secretion associated with a disorder of or injury to the eye is disclosed. The method, which is based on the discovery that conjunctival goblet cell mucous secretion is under the control of the autonomic nervous system, includes administering to an affected eye of a patient a neural system stimulus or inhibitor for sensory, parasympathetic or sympathetic nervous system function. Also disclosed are a therapeutic composition and an article of manufacture including the therapeutic composition useful for carrying out the method of the invention.

7 Claims, 10 Drawing Sheets

OTHER PUBLICATIONS

Carlstedt et al., "*Mucous glycoproteins: A gel of a problem*", Essays Biochem. 20:40–76 (1985).

Carraway et al., "*O–glycosylation pathway for mucin–type glycoproteins*," Bioessays 10:117–121 (1989).

Chao et al., "*Macromolecular components of human ocular mucus,*" In: the Preocular Tear Film in Health, Disease and Contact Lens Wear; edited by FJ Holly. TX: Lubbock, Dry Eye Institute; pp. 331–340 (1986).

Chao et al.,"*Studies on the isolation and composition of human ocular mucin,*" Exp. Eye Res: 47:185–196 (1988).

Dartt et al., "*Stimulation of Rat Conjunctival Goblet Cell Mucus Secretion,*" ARVO Abstracts: Invest. Ophthalmol.Civ. Sci. 31(Suppl):408 (1990).

Davis et al., "*Goblet cell degranulation in isolated canine tracheal epithelium: response to exogenous ATP,ADP, and adenosine,*" Am. J. Physiol. 262:C1313–C1323 (1992).

Denis et al., "*Autoradiographic characterization and localization of vasoactive intestinal peptide binding sites in abino rat and rabbit eyes,*" Exp. Eye Res. 52:357–366 (1991).

Dohlman et al., "*The glycoprotein (mucus) content of tears from normals and dry eye patients,*" Exp. Eye Res. 22:35 9–365 (1976).

Friend et al., "*Conjunctional goblet cell frequency after alkali injury is not accurately reflected by aqueous tear mucin content,*" Invest. Othalmol. Vis. Sci. 24:612–618 (1983).

Geggel et al., "*Removal of viable sheets of conjunctival epithelium with Dispase II,* " Invest. Ophthalmol. Vis. Sci. 26:15–22 (1985).

Gipson, et al., "*Characteristics of a glycoprotein in the ocular surface glycocalyx,*" Invest. Ophthalmol. Vis. Sci. 33:218–227 (1992).

Greiner et al., "*Goblet cells of the human conjunctiva,*" Arch. Opthalmol. 99"2190–2197 (1981).

Greiner et al., "*Histochemical analysis of secretory vesicles in nongoblet conjunctival epithelial cells,*" Acta Ophthalmol. 63:89–92 (1985).

Hoffstein et al., "*Leukotriene $D_4(LTD_4)$ induces mucus secretion from goblet cells in the guinea pig respiratory epithelium,*" Exp. Lung Res. 16:711–725 (1990).

Holly et al., "*Tear physiology and dry eyes,*" Surv. Ophthalmol. 22:69–87 (1977).

Holtzman "*Arachidonic acid metabolism in airway epithelial cells,*" Annu. Rev. Physiol. 54:303–329 (1992).

Huang et al., "*Distribution of conjunctival goblet cells in normal rabbits,*" Invest. Opthalmol. Vis. Sci. 25(Suppl):322 (1984).

Huang et al., "*Morphogenesis of rat conjunctival goblet cells,*" Invest. Ophthalmol. Vis. Sci. 29:969–975. No date given.

Jensen et al., "*Mucosubstances of the acini of the human lacrimal gland (orital part). I. Histochemical identification,*" Acta Ophthalmol. 47:605–619 (1969).

Jumblatt et al., "*Intracellular Mediators of Conjunctival Mucin Secretion,*" ARVO Abstracts. Invest Ophthalmol. Vis. Sci. 34(Suppl): 822 (1993).

Karjalainen et al., "*Catecholamine–containing and acetylcholinesterase–positive nerve fibres in the rabbit conjunctiva,*" Acta Ophthalmol. 56:911–920 (1978).

Kessing, "*Mucous gland system of the conjunctiva,*" Acta Ophthalmol. 46(Suppl 95):9–133 (1968).

Kim et al., "*$P_2$punrinoceptor regulation of mucin release by airway goblet cells in primary culture,*" Br. J. Pharmacal. 103:1053–1056 (1991).

Kinoshita et al., "*Goblet cell density in oscular surface disease. A better indicator than tear mucin,*" Arch Ophthalmol. 101:1284–1287 (1983).

Klyce et al., "*Transport processes across the rabbit corneal epithelium: a review,*" Curr. Eye Res. 4:323–331 (1985).

Kulkarni et al., "*Cyclooxygenase and lipoxgenase pathways in anterior uvea and conjunctiva. In: The Oscular Effects of Prostaglandins and Other Eiconsanoids,*" edited by Bito LX and Stjernshantz J.;Alan R. Liss, Inc; New York,pp. 39–52 (1989).

Kuo et al., "*Capsaicin and sensory neurpeptide stimulation of goblet cells secretion in guinea–pig trachea*"; J. Physiol 431: 629–641 (1990).

Laburthe et al., "*Functional VIP receptors in the human mucus–secreting colonic epithelial cell line CL. 16E,*" Am. J. Physiol. 256:G443–G450 (1989).

Lamberts, "*Physiology of the tear film. In: The Cornea: Scientific Foundations and Clinical Practice,*" edited by Smolen G. and Thoft RA; Little, Brown and Company, Boston pp. 38–52 (1987).

Latkovic, "*The Ultrastructure of the normal conjunctival epithelium of the guinea pig: III. The bulbar zone, the zone of the fornix and the supranodular zone,*" Acta Ophthalmol. 57:305–320 (1979).

Latkovic, "*The ultrastructure of the normal conjunctival epithelium of the guinea pig: IV, The Palpebral and the Perimarginal Zones,*" Acta Ophthalmol. 57321–335 (1979).

Leikauf et al., "*Bradykinin stimulates chloride secretion and prostaglandin $E_2$ release by canine tracheal epithelium,*" Am. J. Physiol. 248:F48–F55 (1985).

Lemp, "*Basic principles and classifcation of dry eye disorders. In: The Dry Eye:A Comprehensive Guide,*" edited by Lemp MA and Marquardt R.; Springer–Verlag: Berlin, pp. 101–132 (1992).

Lencer et al., "*Interaction of cholera toxin with cloned human goblet cells in monolayer culture,*" Am. J. Physiol. 258:G96–G102 (1990).

Luhtala et al., "*Calcitoningene–related peptide immunoreactive nerve fibers in the rat conjunctiva,*" Invest. Ophthalmol. Vis. Sci., 32:640–645 (1991).

Luhtala et al., "*The distribution and origin of substance P immunoreactive fibres in the rat conjunctiva,*" Exp. Eye Res. 53:641–646 (1991).

Macintosh, "*Innervation of the conjunctiva in monkeys: An electron Microscopic and nerve degeneration study,*" Graefes. Arch. Clin. Exp. Ophthalmol. 192:105–116 (1974).

McCool et al., "*The T84 human colonic adenocarcinoma cell line produces mucin in culture and releases it in response to various secretagogues,*" Biochem. J. 267:491–500 (1990).

Merzel et al., "*Origin and renewal of goblet cells in the epithelium of the mouse small intestine,*" Am. J. Anat. 124:281–306 (1969).

Moore et al., "*Density and distribution of canine conjunctival goblet cells,*" Invest. Ophthalmol. Vis. Sci. 28:1925–1932 (1987)

Nelson, et al., "*Conjunctival goblet cell densities in ocular surface disease,*" Arch. Ophthalmol. 102:1049–1051 (1984).

Neutra et al., "Synthesis of the carbohydrate of mucus in the golgi complex as shown by electron microscope radioautography of goblet cells from rats injected with glucose-$H_3$," J. Cell. Biol. 30:119–136 (1966).

Neutra et al., "Regulation of intestinal goblet cell secretion II. A survey of potential secretagogues," Am. J. Physiol. 242;G380–G387 (1982).

Norman et al., "Hormones" Academic Press, Inc.: Orlando, pp. 646–647 (1987).

Parakkal et al., "The fine structure of the lipid droplets in the meibomian gland of the mouse," J. Ultrastruct. Res. 10:417–421 (1964).

Payne et al., "Parietal cell preparation and arachidonate metabolism," Methods Enzymol. 187:505–513 (1990).

Phillps et al., "Both crypt and villus intestinal goblet cells secrete mucin in response to cholinergic stimulation," Am. J. Physiol. 262:G327–G331 (1992).

Phillips et al., "Regulation of intestinal goblet cell secretion III. Isolated intestinal epithelium," Am. J. Physiol. 247:G674–G681 (1984).

Phillips et al., "Regulation of intestinal goblet cell secretion IV. Electrical field stimulation in vitro," Am. J. Physiol. 247:G682–G687 (1984).

Piomelli et al., "Lipoxygenase metabolites of arachidonic acid in neuronal transmembrane signalling," Trends in Pharm. Sci. 11:367–373 (1990).

Rieves et al., "Airway epithelial cell mucin release: immunologic quantitation and response to platelet–activating factor," Am. J. Respir. Cell. Mol. Biol. 6:158–167 (1992).

Roomi et al., "Cholera–induced mucin secretion from rat intestine: lack of effect of cAMP, cycloheximide, VIP, and colchicine", Am. J. Physiol. 247:G140–G148 (1984).

Roth "Cytochemical localization of terminal N–acetyl–D–Galactosamine residues in cellular compartments of intestinal goblet cells; implications for the topology of O–glycosylation," J. Cell Biol. 98:399–506 (1985).

Ruskell "Innervation of the conjunctiva," Trans. Opthalmol. Soc. UK 104:390–395 (1985).

Shellans et al., "Conjunctival goblet cell response to vasoconstrictor use," J. Ocular Pharm. 5:217–220 (1989).

Smith et al., "Biosynthesis and secretion of human colonic mucin glycoproteins," J. Clin. Invest. 80:300–307 (1987).

Smith "The eicosanoids and their biochemical mechanisms of action, Biochem. J. 259:315–324 (1989).

Sommer et al., "Goblet cell response to vitamin A treatment for corneal xerophthalmia," A. J. Ophthalmol. 94:213–215 1982).

Specian et al., "Mechanism of rapid mucus secretion in goblet cells stimulated by acetylcholine," J. Cell Biol. 85:626–640 (1980).

Specian et al., "Regulation of intestinal goblet cell secretion I. Role of parasympathetic stimulation," Am. J. Physiol. 242:G370–G379 (1982).

Specian et al., "Functional biology of intestinal goblet cells, Am. J. Physiol. 260:C183–C193 (1991).

Specian et al., "Cytoskeleton of intestinal goblet cells in rabbit and monkey," The Theca, Gastroenterology 87: 1313–1325 (1984).

Specian et al., Recovery of goblet cells from an accelerated secretory event," Anat Rec. 226:97A (1990).

Srinivasan et al., In: Ocular Anatomy, Embryology and Teratology; edited by FA Jakobiec. Philadelphia; Harper and Row, pp. 733–760 (1982).

Srinivasan et al., The conjunctival epithelium, II. Histochemical and ultrastructural studies on human and rat conjunctive," Ophthalmic Res. 9:65–79 (1977).

Stone, RA, "Vasoactive intestinal polypeptide and the ocular innervation," Invest. Ophthalmol. Vis.Sci. 27:951–957 (1986).

Stone et al., "Regulatory peptides in the eye," Experientia 43:791–800 (1987).

Tanelian, DL, "Cholinergic activation of a population of corneal afferent nerves," Exp. Brain Res. 86: 414–420 (1991).

Tinsley et al. "Purification, characterization and localization of neuropeptides in the cornea," Peptides 9: 1373–1379 (1989).

Tokuyama et al., "Neural control of goblet cell secretion in guinea pig airways," Am. J. Physiol. 259:L108–L115, (1990).

Tseng et al., "Goblet cell density and vascularization during conjunctival transdifferentiation," Invest. Ophthalmol. Vis. Sci. 25:1168–1176 (1984).

Unger et al., "Substance P., vasoactive intestinal polypeptide (VIP) and somatostatin levels in ocular tissue of normal and sensorily denervated rabbit eyes," Exp. Eye Res. 32:797–801 (1981).

Verdugo, P., "Goblet cells secretion and mucogenesis," Annu. Rev. Physiol. 52:157–176 (1990).

Woodward, et al., "Studies on the ocular pharmacology of prostaglandin $D_2$" Invest. Ophthalmol. Vis. Sci. 31:138–146 (1990).

Presti, et al., "Receptor antagonists for gastrointestinal peptides" Invited Review pp. G399–G406 (1993).

Goodman and Gilman's; "The Pharmacological Basis of Therapeutics" 7th Edition, Macmillan Publishing Company, New York pp. xi–xiii and p. 92 (1985).

Calbiochem Biochemical/Immunochemical Catalog, pp. 496, 501, 504, 509, and 510 (1992).

*Neurochemicals for the Neuroscientist Catalog/Handbook* Research Biochemicals Inc.; pp. vii–xxii (1992–93).

THERAPEUTIC REGULATION OF ABNORMAL CONJUNCTIVAL GOBLET CELL MUCOUS SECRETION

GOVERNMENT RIGHTS

Part of the work leading to this invention was carried out with United States government funds. Therefore, the U.S. Government has certain rights in this invention.

FIELD OF THE INVENTION

This invention relates to treating aberrant conjunctival goblet cell mucous secretion in connection with disorders of or injuries to the eye.

BACKGROUND OF THE INVENTION

The tear film, ubiquitously present over the surface of the eye, is composed of an overlying lipid layer, a substantial middle aqueous component and an underlying mucous foundation. The mucous layer provides constant protection to the surface of the eye, and stability to the tear film. A rapid release of mucus in response to surface irritants, trauma, or toxins (bacterial and environmental) is necessary to replenish the mucous layer and protect the ocular surface.

Goblet cells of the conjunctiva are the primary source of mucus (complex glycoprotein) that constitutes the inner, mucous layer of the tear film. Regulation of normal goblet cell maturation and turnover, as well as goblet cell mucous synthesis and mucous secretion (mucous production), is important for the health of the ocular surface. In diseases such as keratoconjunctivitis sicca (KCS), Sjögren's Syndrome, vitamin A deficiency, anesthetic cornea, Stevens-Johnson Syndrome, thermal burns, chemical burns, cicatricial ocular pemphigoid, inactive trachoma, drug induced pseudopemphigoid, atopic diseases, radiation keratoconjunctivitis sicca, and superior limbic keratitis there is an alteration in goblet cell maturation, a disruption of mucous production, and a change in the mucous layer (41,49). Effective treatments for these diseases have not yet been developed because so little is known about the conjunctival goblet cell itself or about its secretory functions.

Goblet cells, which are highly polarized exocrine cells identified by their extensive apical accumulation of large secretory granules, are interspersed among the stratified epithelium of the conjunctiva. In the rat, goblet cells occur singly as well as in clusters of variable number (25,26,30,38,48). In humans, goblet cells generally occur singly, and, in addition, some goblet cells tend to group into mucous crypts of varying design in all areas of the conjunctiva (20,30). The intra-epithelial mucous crypts, in particular, closely resemble the clusters of goblet cells found in rat (30). The number of goblet cells per unit area (density) varies from bulbar to tarsal conjunctiva and from nasal to temporal areas in all species studied (25,26,30,38,48).

Goblet cells synthesize and secrete high molecular weight glycoproteins called mucins or mucus (11,50). When secreted, these mucins hydrate and gel, producing a protective mucous blanket covering the ocular surface. The mucous layer contains other components such as water, electrolytes, immunoglobulins (especially IgA), and enzymes. The non-mucin components of the mucous layer are secreted by the stratified squamous epithelial cells of the ocular surface and by the orbital glands. The mucous layer constitutes a physical and chemical barrier that protects the conjunctival and corneal epithelium from bacteria, from bacterial and environmental toxins, and from foreign bodies (37). The mucous layer stabilizes the tear film, prevents desiccation, and provides an optically smooth corneal surface by filling in surface irregularities (37), which is important for good visual acuity.

Little is known about the life cycle of the conjunctival goblet cell. It has been hypothesized, but not proven, that in the rat, goblet cells which form a cluster develop from a single stem cell of unknown location (26). These stems cells have not been found, nor has an immature conjunctival goblet cell been identified, as has been in the colon (70). Thus, the length of the goblet cell life span and the rate of goblet cell turnover have not been determined in the conjunctiva, although basal epithelial cells reach the conjunctival surface in 3–6 days (72). In the intestine, goblet cells mature from stem cells at the base of the crypt and live for 2–3 days (70). During this time, they migrate from crypt base to villus tip, a situation that does not occur in the conjunctiva. In the trachea, goblet cells may differentiate from serous epithelial cells (6) and their life span is longer.

Mature goblet cells display typical characteristics in all tissues studied, being large unicellular glands found in the surface of the epithelium and probably reaching to the basement membrane (72). They are connected by tight junctions to neighboring epithelial cells or other goblet cells and thus are polarized unicellular glands containing the biosynthetic enzymes for unidirectional synthesis and secretion of mucins. The synthetic pathway for mucin secretion by intestinal goblet cells has been demonstrated (50). The basal region of the cell contains the nucleus, mitochondria and rough endoplasmic reticulum (RER). The protein backbone of mucin is synthesized in the RER. The protein is then transported to the golgi apparatus, which is located above the nucleus. In the stacks of the golgi apparatus, the stepwise addition of carbohydrates to the protein backbone occurs as glycosyltransferases are compartmentalized in the golgi stacks (61). The synthesized mucins are then stored in condensed form in mucin granules that each are surrounded by membrane. The secretory granules fill the apical portion of the cell, and the large volume of apical secretory granules gives the goblet cell its distinct shape and appearance. Mucin secretion occurs by fusion of the mucin granule membrane with the apical plasma membrane, releasing the granule contents onto the ocular surface (67). Granule-granule fusion (compound exocytosis) can also occur and is the major type of fusion in stimulated secretion.

Two types of mucous secretion can occur, slow continual baseline or rapid accelerated secretion. In rabbit colon, in the absence of irritants or neurotransmitters, there is slow continual, baseline secretion (70) which represents periodic exocytosis of one or two mucin granules. Only a certain portion of the secretory granules participate in baseline secretion, those located on the periphery of the cell. It is not known what regulates this type of secretion. Nor is it known if this type of secretion occurs in conjunctival goblet cells or a population of conjunctival goblet cells.

In the intestine and colon, secretion of the entire goblet cell mucin contents can occur in a matter of minutes in response to a variety of stimuli (70). Secretion is an orderly series of membrane fusion events, which begins at the apical plasma membrane, proceeds first to the most central mucous granules and is then propagated to include peripheral mucous granules, and finally spreads to the most basal mucous granules until most of the granules have been secreted (67,70). This produces the cavitation typical of a stimulated intestinal epithelium. In this rapid secretion, the mucin granule membranes are not recycled, but are lost. The remaining goblet cell, however, maintains its shape and within 30 minutes the intracellular mucin is resynthesized (70,71). Again, little is known about the mechanism of mucous secretion in conjunctival goblet cell. A stimulated conjunctiva can have a cavitated appearance similar to that of the intestine, suggesting all or none secretion, but this has not been studied systematically. Nor is it known if conjunctival goblet cells resynthesize their mucins or instead are desquamated after secreting once.

Regulation of the mucous layer may require an extremely complex process, controlled at several different levels. A crucial question in the regulation of mucin secretion is what are the extracellular and intracellular signals that cause mucin granule fusion with the apical membrane. Baseline secretion and accelerated secretion appear to be regulated by different mechanisms. To date, the signals for baseline secretion are not known, but they have been identified for accelerated secretion in some tissues (70). In the intestine, electric field stimulation, parasympathetic nerves and muscarinic agonists stimulated crypt goblet cell mucin secretion (56,57,68). Because electric field stimulation of secretion was not completely blocked by the muscarinic antagonist atropine, a second, as yet unidentified, agonist exists that causes intestinal goblet cell secretion (57).

In addition to cholinergic agonists, neurotensin, which like cholinergic agonists causes an increase in intracellular $[Ca^{2+}]$, increases intestinal goblet secretion (4). The role for agonists that increase intracellular levels of cAMP in stimulating intestinal goblet cell secretion remains controversial. Cholera toxin, which constitutively activates adenylate cyclase to produce cAMP, only indirectly stimulates mucin secretion, but the mediator is not known (60). The role of Vasoactive Intestinal Peptide (VIP), a cAMP-dependent agonist, varies between studies. In some intestinal or colonic goblet cell lines, VIP stimulates secretion (46); in some lines, VIP does not itself stimulate secretion, but potentiates the effect of cholinergic agonists (41); and finally in other cell lines and in vivo, it has no effect (42,51,60). Thus, in the intestine and colon cholinergic agonists and neurotensin, both of which increase intracellular $[Ca^{2+}]$, appear to be the major stimuli of goblet cell mucin secretion. However, agonists such as VIP, which increase cAMP, appear to have a minor role, if any, in causing intestinal or colonic goblet cell secretion.

In the trachea, it has been shown recently that there are several different agonists that each stimulate goblet cell secretion. Cholinergic agonists using muscarinic receptors; ATP using purinergic, $P_2$ receptors; Substance P, neurokinin A and neurokinin B using neurokinin $NK_1$ receptors; calcitonin gene-related peptide; leukotriene $D_4$; and platelet-activating factor each causes goblet cell secretion (14,22, 31,35,59,78). The second messenger for these agonists is most likely $Ca^{2+}$, although this has yet to be measured.

Studies performed to examine conjunctival goblet cell mucous secretion have been inconclusive. In one study mucin discharge was stimulated 2–3 fold by 8-Br-cGMP but was unaffected by 8-Br-cAMP (28). In another, 16,16-dimethylprostaglandin $E_2$ (dmPGE$_2$), which can increase cAMP levels, was shown by electron microscopy to cause fusion of individual conjunctival goblet cell mucin granules and subsequent discharge of their contents onto the ocular surface (3,13). However, it has also been shown that high $[K^+]$, which is known to cause neural stimulation in tissues in general, does not stimulate goblet cell mucous secretion. Physical manipulation of the eye itself will cause the conjunctival goblet cells to secrete mucus (13).

Normal maturation of goblet cells and normal goblet cell mucin production are important for the health of the ocular surface. Either an increase in mucous secretion and/or in goblet cell maturation, or a decrease in mucous secretion and/or in goblet cell maturation can cause ocular surface problems. An increase in mucus in the tear film occurs in vernal conjunctivitis, giant papillary conjunctivitis, and irritation or injury to the ocular surface (2). A decrease in mucus or change in the character of mucus in the tear film occurs in diseases such as keratoconjunctivitis sicca (KCS), S öSgren's Syndrome, vitamin A deficiency, anesthetic cornea, Stevens-Johnson Syndrome, cicatricial ocular pemphigoid, inactive trachoma, thermal burns, chemical burns, drug induced pseudopemphigoid, atopic diseases, radiation KCS, and superior limbic keratitis (16,17,32,41,49,51,66). In KCS and Sjögren's Syndrome, there is a decrease in goblet cell number and an increase in mucus strands in the tear film (41); however, the presence of such strands indicates decreased clearance of mucus and not increased mucous secretion.

That both an increase or a decrease in the mucous layer can disrupt the ocular surface suggests that the mucous layer is tightly regulated. This regulation could be occurring at many levels—from the central nervous system, to the conjunctival epithelium (including goblet cell and stratified squamous cell secretion), to the goblet cell itself, to the tear film. Currently, there are no ways to clinically evaluate the mucous layer, mucin secretion, mucin synthesis, or goblet cell maturation to determine at which level the regulation has broken down, creating the disease process. The availability of methods to evaluate the state of conjunctival goblet cells and of methods of either stimulating or inhibiting mucous secretion as appropriate would go far in providing ways of diagnosing and treating ocular injuries or diseases and maintaining the health of the ocular surface.

SUMMARY OF THE INVENTION

The invention is based on the unexpected discovery that conjunctival goblet cell mucous secretion is under the control of the sensory nervous system, responding to both direct and indirect neuronal stimulation. Thus, topical (or local, e.g., subconjunctival) application of therapeutic compositions that include stimuli or inhibitors to sensory, parasympathetic and sympathetic nervous system function can stimulate or block, as appropriate, conjunctival goblet cell mucous secretion and relieve the unpleasant and uncomfortable symptoms of aberrant mucin production.

The invention generally features a method of treating patients suffering from aberrant conjunctival goblet cell mucous secretion associated with a disorder of or injury to the eye, including treating any condition in which the patient is bothered by an excess or lack of mucous production. The steps of the method include providing a therapeutic composition comprising a neural system stimulus or inhibitor (i.e., stimulus or inhibitor to sensory, parasympathetic or sympathetic nervous system function) selected from the group consisting of adrenergics, cholinergics, dopaminergics, serotonergics, neuropeptides, neurotoxins, ion channel modulators and local anesthetics, in a pharmaceutically acceptable carrier substance; and administering a therapeutically effective amount of the composition to an affected eye of a patient. Also featured are a therapeutic composition and an article of manufacture including the therapeutic composition useful for carrying out the method of the invention. The article of manufacture includes packaging material and the therapeutic composition described above contained within the packaging material. As described, the therapeutic composition is therapeutically effective for controlling aberrant conjunctival goblet cell mucous secretion. The packaging material includes a label that indicates that the therapeutic composition can be used for controlling aberrant conjunctival goblet cell mucous secretion associated with a disorder of or injury to the eye.

The active agent in the therapeutic composition, if a neural system stimulus, is preferably selected from the group that includes adrenergic agonists (e.g., phenylephrine, epinephrine, clonidine, isoproterenol or methoxamine); cholinergic agonists (e.g., carbachol, pilocarpine, muscarine or bethanechol); dopaminergic agonists (e.g., dopamine, mesulergine or apomorphine); serotonergic agonists (e.g., serotonin, urapidil, quipazine or α-methylserotonin); neuropeptidergic agonists (e.g., Vasoactive Intestinal Peptide or Substance P); and ion channel modulators (e.g., the calcium channel stimulator BAY K 8644, the sodium channel stimulator veratridine or the potassium channel stimulator minoxidil). When the active agent is a neural system inhibitor, it is preferably selected from the group consisting of adrenergic antagonists (e.g., prazosin, phentolamine, timolol, phenoxybenzamine, pindolol, yohimbine, propranolol or ICI-118, 551); cholinergic antagonists (e.g., atropine, tubocurarine or scopolamine); dopaminergic antagonists (e.g., haloperidol or trifluoperidol); serotonergic antagonists (e.g., methysergide); neuropeptidergic antagonists (e.g., [4-Cl-D-Phe$^6$, Leu$^{17}$]-Vasoactive Intestinal Peptide, VIP-(10–28), [D-Arg$^1$, D-Phe$^5$,D-Tryp$^{7,9}$, Leu$^{11}$]-Substance P or spandide II); neurotoxins (e.g., botulinus toxin); ion channel modulators (e.g., the calcium channel blocker verapamil, the sodium channel blocker conotoxin or the potassium channel blocker tetraethylammonium chloride or quinine); and local anesthetics, (e.g., lidocaine).

The classifications listed above for neuronally active agents are well known to those of skill in the art and are described, for example, in Goodman and Gilman, *The Pharmacological Basis of Therapeutics,* MacMillan Publishing Co., New York (1985); in the neurochemical catalog/handbook of Research Biochemicals, Inc., Natick, Mass.; and in the biochemical/immunochemical catalog of Calbiochem, San Diego, Calif. The examples given of specific agents are exemplary only and in no way are intended to limit the scope of the therapeutic methods or therapeutic compositions of the invention.

It is most preferred that the method of the invention be used to treat a human patient, preferably by topical administration of the therapeutic composition to the ocular surface. Alternatively, the therapeutic composition can be applied subcutaneously, to a region of the eye adjacent the ocular surface.

In another aspect, the invention features a method of retaining conjunctival goblet cells in an unstimulated state with the administration of a local anesthetic or other inhibitor in order, e.g., to perform a biopsy on an afflicted patient and examine the sampled tissue for diagnosis of disease. Goblet cells in sampled tissue could be examined by Alcian blue/PAS stain, stains used for impression cytology, lectins, monoclonal and polyclonal antibodies or other markers of goblet cells. Nerves could be examined in sample tissue by monoclonal and polyclonal antibodies, histochemical techniques, or other markers of neural tissue. Sampled tissue could be removed and goblet cell secretion stimulated in vitro, goblet cells and conjunctiva could be cultured for subsequent study, or goblet cells could be purified for subsequent culture, physiological study, biochemical study, or histochemical study.

Alternatively, a biopsied sample could be examined for efficacy of treatment. The patient could be treated with a candidate therapeutic agent or a sensory stimulus to the ocular surface before administration of the local anesthetic or other inhibitor, which would stop any further change in conjunctival goblet cell mucous secretion. In this way, the effect of the candidate agent on a specific patient and the number of functioning goblet cells could be determined. One eye could be stimulated and the other unstimulated as a contralateral control and then the two compared. These methods could be performed at 1–2 week intervals to test the efficacy of therapeutic treatments on goblet cell number, number of functioning goblet cells or other parameters, or to classify the type of disorder.

Other features and advantages of the invention will be apparent from the following description of the preferred embodiments thereof and from the claims.

DESCRIPTION OF THE PREFERRED EMBODIMENT

The invention is based on the discovery that stimulation of reflex afferent sensory nerves, e.g., by corneal debridement, causes significant conjunctival goblet cell mucous secretion. In addition, topical application of VIP, carbachol (carbamyl choline chloride), serotonin, epinephrine, dopamine or phenylephrine also stimulates conjunctival goblet cell mucous secretion. Therefore, parasympathetic, serotonergic, dopaminergic, peptidergic and sympathetic nerves are involved in the efferent arm of the reflex pathway. Thus, conjunctival goblet cell mucous secretion is under the control of the autonomic nervous system, responding to both direct and indirect stimulation.

Without being bound by any theory, it appears from our discoveries that sensory stimuli arising in the conjunctiva and cornea activate the afferent sensory trigeminal nerve, which then reflexively activates the efferent parasympathetic and sympathetic nerves innervating the stroma and epithelial parts of the conjunctiva. Goblet cells could be directly innervated and/or neurotransmitters could be released in close enough proximity to the goblet cells to be effective at stimulating mucous secretion. We conclude that topical (or local, e.g., subconjunctival) application of therapeutic compositions that include stimuli or inhibitors to sensory, parasympathetic and sympathetic nervous system function can stimulate or block, as appropriate, conjunctival goblet cell mucous secretion and relieve the unpleasant and uncomfortable symptoms of aberrant mucin production.

Figure 1:
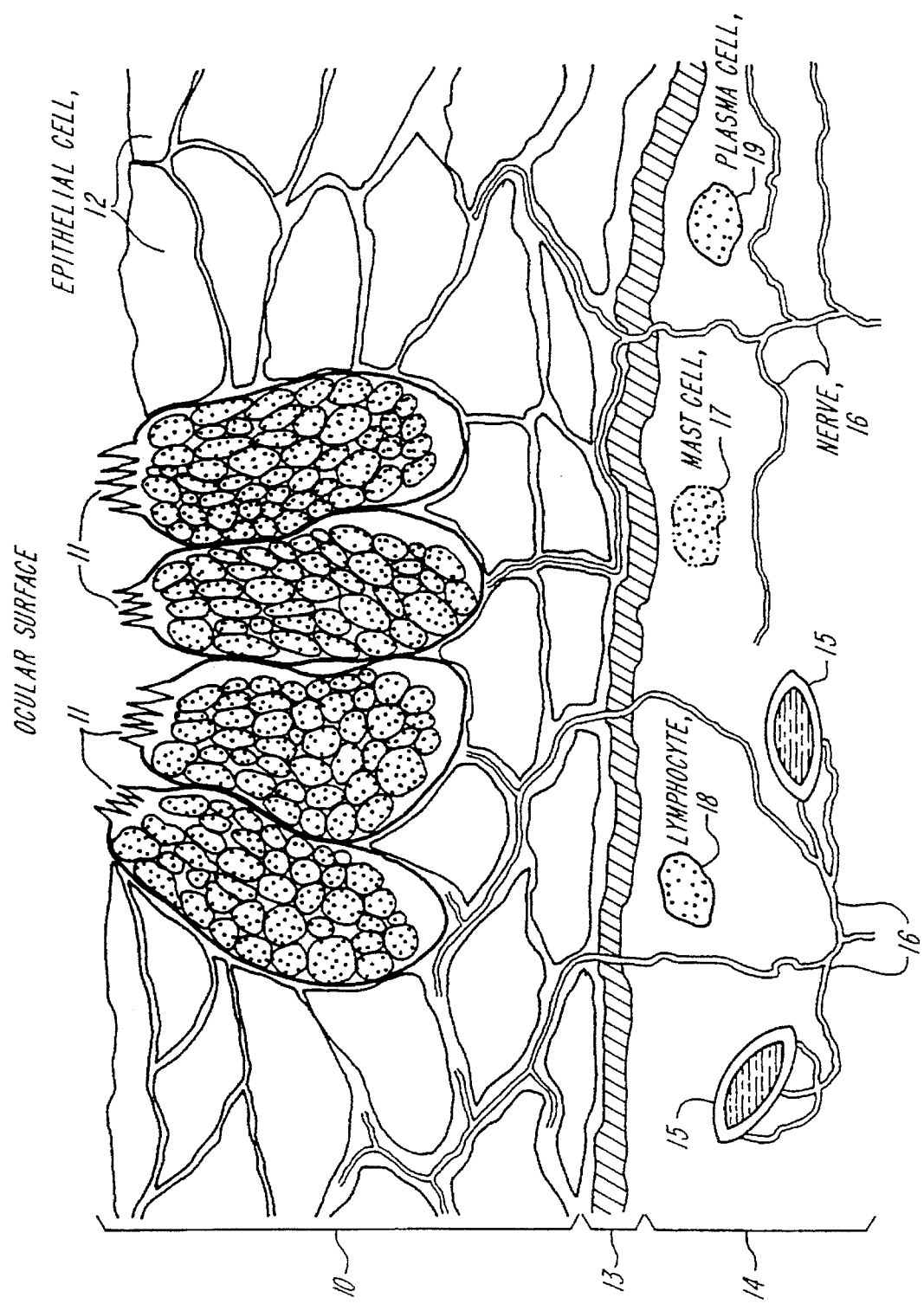
FIG. 1 is a schematic drawing of a section through the eye, showing components that could participate in regulation of conjunctival goblet cell mucous secretion.

Referring to FIG. 1, a schematic drawing of a section through the eye, goblet cells 11 are present in the superficial layer of the conjunctiva 10 adjacent to squamous epithelial cells 12. Underneath the goblet cells and squamous epithelial cells is an undulating basement membrane 13 which attaches these cells to the underlying stroma 14. The stroma is loose connective tissue which contains blood vessels 15, nerves 16, mast cells 17, lymphocytes 18, and plasma cells 19.

Figure 2A:
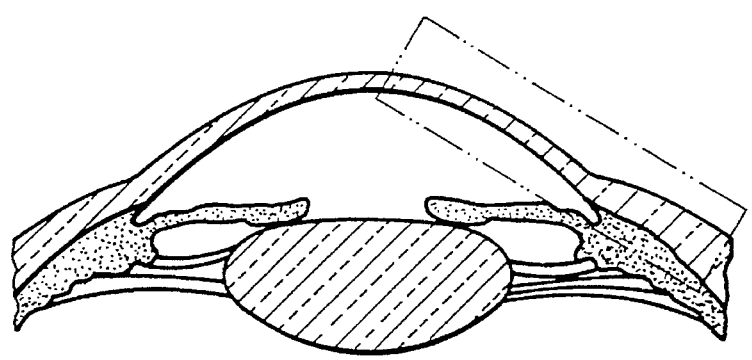
FIG. 2A is a schematic drawing of a section through the the entire eye.
Figure 2B:
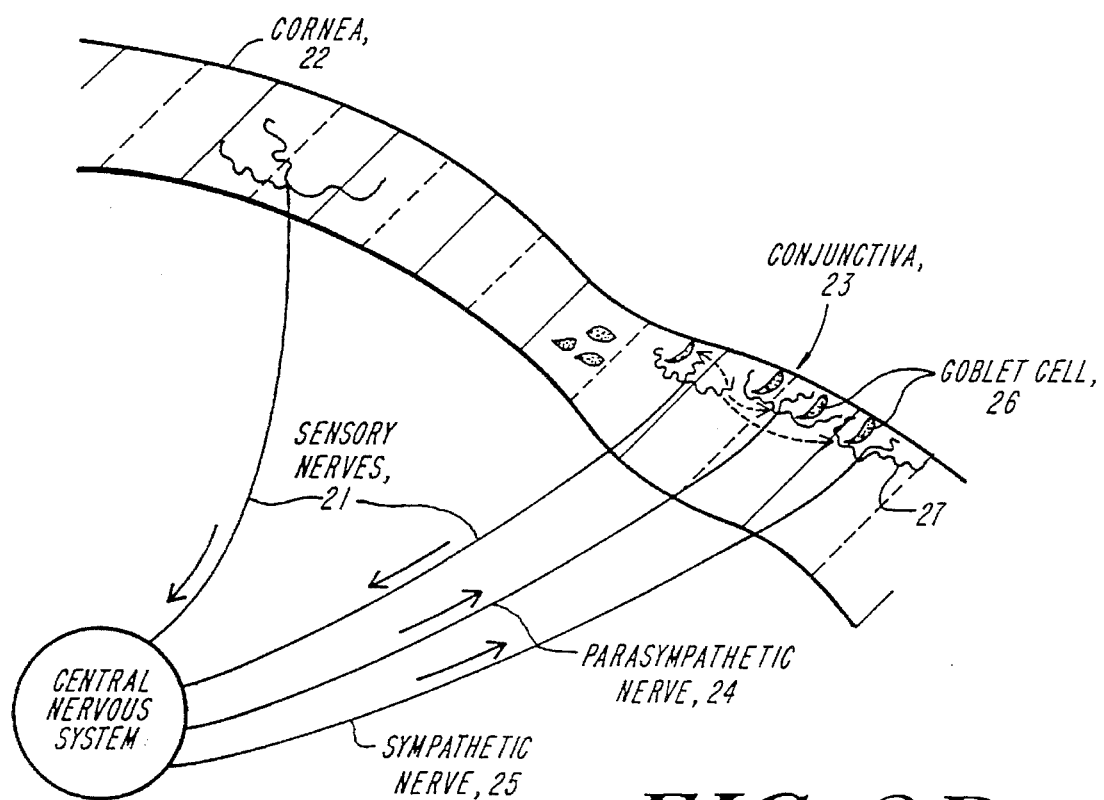
FIG. 2B is a schematic drawing of an expanded region of FIG. 2A showing the neural pathways that could participate in regulation of conjunctival goblet cell mucous secretion.

Referring to FIG. 2, a schematic drawing of the neural innervation of the conjunctiva controlling goblet cell mucous secretion, stimulation of sensory nerves 21 present in the cornea 22 or conjunctiva 23 would cause activation of the parasympathetic 24 and sympathetic 25 nerves that innervate the conjunctiva, which includes the goblet cells 26, resulting in increased goblet cell exocytosis of mucin. In addition, stimulation of sensory nerve endings in the conjunctiva 27 would cause retrograde release of neurotransmitters that stimulate the goblet cells. In a parallel fashion, inhibition of nervous system function would result in reduced goblet cell mucous secretion.

There are three possible mechanisms by which nerves could stimulate conjunctival goblet cell mucous secretion. First, the nerves innervating goblet cells could directly stimulate the goblet cells to secrete mucus. Second, nearby nerve endings innervating non-goblet cells could release neurotransmitters that could diffuse to goblet cells and stimulate them to secrete mucus. Third, nerves could innervate non-goblet cells such as fibroblasts, melanocytes, macrophages, mast cells, lymphocytes, and plasma cells (72) and stimulate one or more types of these cells, which then could release biologically active peptides, vasoactive amines, eicosanoids, or other compounds that could diffuse to goblet cells and stimulate them to secrete mucus. The first two modes of stimulation are direct; the third mode is indirect, requiring action through a second compound. The latter two proposed modes of stimulation would function because the conjunctival epithelium is a leaky epithelium and has, resting in very loose connective tissue called the substantia propria, wide intercellular spaces affording opportunity for diffusion of neurotransmitters and peptides from stroma to epithelium or within the epithelium (72).

To date, the sensory neurotransmitters calcitonin gene-related peptide (CGRP) and Substance P (Sub P) have been identified in the conjunctiva (43,44,77). In addition to the classical neurotransmitters acetylcholine and norepinephrine, the sensory, sympathetic and parasympathetic nerves contain the neuropeptide VIP (8,80). There are also VIP-binding sites, probably receptors, in the conjunctiva (15).

The conjunctiva contains little or no somatostatin or bombesin (80). The nerves innervating the limbal blood vessels which border the conjunctiva contain several neuropeptides including CGRP, Sub P, neuropeptide Y, VIP, and galanin (75). Because of the limited number of studies identifying neuropeptides in the conjunctiva, it is likely that there are several additional peptides present that have yet to be identified.

In summary, both direct neural stimulation of goblet cells or direct stimulation by diffusion of neurotransmitters from nearby nerve endings can occur. In addition, indirect paracrine stimulation of goblet cells is also possible.

As has been described, mucin disorders can be classified into two general categories, depending on whether an increase or decrease in mucous secretion is observed. In the first category (Group A) vernal conjunctivitis, giant papillary conjunctivitis, and irritation or injury to the ocular surface have been shown to result in an increase in mucus in the tear film (2), A decrease in mucous secretion is observed in the diseases or conditions classified in Group B, e.g., vitamin A deficiency, cicatricial ocular pemphigoid, drug induced pseudopemphigoid, inactive trachoma, Stevens-Johnson Syndrome, thermal and chemical burns, radiation keratoconjunctivitis sicca, atopic diseases, superior limbic keratoconjunctivitis, and keratoconjunctivitis sicca (KCS) (41,49). (Mucus strands have been reported in the tear film in patients with KCS (41); however, the presence of such strands indicates decreased clearance of mucus and not increased mucous secretion.)

We have determined that sensory corneal stimulation (corneal debridement) causes conjunctival goblet cell mucous secretion and that this stimulus is blocked by the local anesthetic lidocaine. Therefore, neural activation was shown to stimulate conjunctival goblet cell mucous secretion. In a parallel manner, based on the properties of nerves in general, ion channel blockers, neurotoxins, and local anesthetics should inhibit conjunctival goblet cell secretion and ion channel activators should stimulate this secretion. We have also found, by determining the effect of topical application of agents to the rat eye and by measuring the number of remaining goblet cells that still contain mucus, that the adrenergic agonists epinephrine and phenylephrine, the cholinergic agonist carbachol, the dopaminergic agonist dopamine, the serotonergic agonist serotonin, and the peptidergic agonists VIP and Sub P stimulate conjunctival goblet cell secretion. Based on the properties of the receptors for these compounds, the corresponding antagonists, i.e., specific adrenergic, cholinergic, dopaminergic, serotonergic, and peptidergic antagonists, could prevent goblet cell secretion. An expanded discussion of these experimental findings will be found in the examples.

To summarize our findings, the mucin disorders involving excess mucous secretion are treated by applying an inhibitor of the sensory, parasympathetic or sympathetic nervous system to the affected eye of the patient. These inhibitors can include adrenergic, cholinergic, dopaminergic, serotonergic or peptidergic antagonists; local anesthetics; neurotoxins; and ion channel blockers, for example. Nervous system stimuli are used in therapeutic treatment of patients with depressed levels of mucous secretion. Such stimuli include the adrenergic, cholinergic, dopaminergic, serotonergic or peptidergic agonists; and ion channel stimuli. The treated disorders include any condition in which a patient is bothered by an excess of or a lack of mucous production, e.g., conditions that would interfere with contact lens wear.

A rat model system developed to permit gross evaluation of potential active agents will be described below in Example I. Candidate agents chosen in such a model system can be examined to determine the extent of their effectiveness for a specific patient in a simple assay (shown in Example III) using the patient's untreated eye as an internal control.

The therapeutic agents may be administered (alone or in combination) topically or parenterally, (e.g., intranasally, subcutaneously, subconjunctivally or retrobulbarly) by routine methods in pharmaceutically acceptable inert carrier substances. Optimal dosage and modes of administration can readily be determined by conventional protocols. For example, the therapeutic agents may be administered topically to the eye as a drop, or within ointments, gels, or liposomes. Further, they may be infused into the tear film by means of a pump-catheter system. In other embodiments, the therapeutic agents may be attached to and/or incorporated into or carried by contact lenses or contained within continuous or other selective-release devices including membranes, and thereby contact the ocular surface. The dosage of therapeutic agent is that dosage which is effective in alleviating the indicated symptoms, e.g, a solution of active agent at a concentration of $10^{-8}$–$10^{-2}$M as specifically determined for each agent, and most preferably $10^{-6}$–$10^{4}$M, applied as a drop of about 50 µl.

The following examples are presented to illustrate the advantages of the present invention and to assist one of ordinary skill in making and using the same. These examples are not intended in any way otherwise to limit the scope of the disclosure.

EXAMPLE I

Development of a Model System to Measure Regulation of Conjunctival Goblet Cell Mucous Secretion in vivo We have developed a method of applying stimuli and inhibitors to the eye and removing conjunctival tissue in an in vivo rat model that results in minimal manipulation of the ocular surface, minimal non-specific stimulation of mucous secretion and is specific for goblet cell mucous secretion. Thus, the in vivo rat model can be used to study conjunctival goblet cell mucous secretion. With this model, the ocular surface of anesthetized rats is treated topically or subconjunctivally. After treatment, the animals are euthanized, the ocular surface is fixed, conjunctival tissue is removed and mucus in the secretory granules of goblet cells stained with alcian blue and periodic acid-Schiff's (PAS) reagents to indicate mucin-containing goblet cells. The number of mucin-containing goblet cells is then determined. A decrease in the number of mucin-containing goblet cells indicates an increase in goblet cell secretion. Using this model system, the effect of buffer composition on conjunctival goblet cell mucous secretion was tested, as was the effect of topically applied prostaglandin $E_2$ analog, dmPGE$_2$ and adrenergic agonist, epinephrine.

Mucous secretion from superior and inferior conjunctiva did not significantly change with anesthesia or when the tear [$K^+$] was varied from 4.0 to 37.4 mM. However, the inferior conjunctiva contained significantly higher alcian blue-PAS-stained goblet cell density than the superior conjunctiva.

Goblet cell mucous secretion from the inferior conjunctiva was stimulated by topical prostaglandin $E_2$ analog and epinephrine. The prostaglandin $E_2$ analog 16,16-dimethyl-prostaglandin $E_2$ (dmPGE$_2$) at 100 µM increased goblet cell mucous secretion from inferior but not superior conjunctiva. The adrenergic agonist, epinephrine at 100 µM stimulated mucous secretion. Electron microscopy confirmed the stimulation of mucous secretion with dmPGE$_2$ and epinephrine.

MATERIALS AND METHODS

Materials 16,16-dimethyl-prostaglandin $E_2$ and (−)-epinephrine (bitartrate salt) were obtained from Sigma (St. Louis, Mo.); all other chemicals from Sigma or Fisher (Pittsburgh, Pa.) unless indicated otherwise.

Animals

Male Sprague-Dawley rats at 12 weeks of age (young adults) (Charles River Laboratories, Wilmington, Mass. and Taconic Laboratory Animals, Germantown, N.Y.) were euthanized with intraperitoneal pentobarbital (1300 mg/kg) or anesthetized with intraperitoneal injection of 100 mg/kg ketamine and 6.7 mg/kg acepromazine, then treated and euthanized. All experiments conformed to the ARVO Resolution on the Use of Animals in Biomedical Research.

Measurement of Goblet Cell Mucous Secretion

To determine the effect of topically applied solutions, experimental solutions (20 µl drops) were placed on each eye from the temporal region every 20 min for 1 hr. The solutions were carefully removed with a cotton-tipped applicator from the nasal region of the eyes before placement of the next drop or before euthanization. The animals were euthanized and the eyes were fixed with half-strength Karnovsky's solution (2.5% glutaraldehyde and 2% paraformaldehyde in cacodylate buffer). Because conjunctival goblet cell density is not uniform throughout the conjunctiva, care was taken to use a specific area for sampling. To mark the area for sampling, a 2-mm trephine was placed adjacent to the limbus at the central superior bulbar and central inferior bulbar conjunctival locations to obtain conjunctival buttons. Conjunctival buttons were then dissected and tissue placed epithelial side up on gelatin-coated, glass microscope slides. These flat-mount preparations were then fixed overnight with 65% ethanol, 5% acetic acid, and 2% formaldehyde. Mucin contained in the secretory granules of the goblet cells was stained with alcian blue and periodic acid-Schiff (PAS) stain (79). The number of mucin-containing goblet cells was counted in a masked fashion using light microscopy (standard Zeiss microscope) at 160× magnification. The density of mucin-containing goblet cells was determined by averaging counts of goblet cells in three 0.16 mm² areas in each button. A decrease in mucin containing goblet cell number per unit area (density) indicated an increase in mucous secretion.

Scoring parameters

The mucin-containing goblet cells stained purple and fuchsia with alcian blue and PAS, respectively. By focusing through the tissue, cells with moderate to intense staining and sharp, defined cell borders were considered non-secreted and were counted. Cells with very light stain, absence of color, indistinguishable color from background staining and fuzzy borders were considered cells that had secreted mucus and were not counted. Following these criteria, the non-secreted mucin-containing goblet cells in the three 0.16 mm² areas were counted, averaged and expressed as mucin-containing goblet cell density. Therefore, a decrease in mucin-containing goblet cell density indicated mucous secretion.

Solutions for Topical Application

Krebs-Henseleit Buffer (KHB) contained (mM) 115.0 NaCl, 25.0 NaHCO$_3$, 4.0 KCl, 1.0 MgCl$_2$, 0.5 NaH$_2$PO$_4$, 1.1 CaCl$_2$, and 5.5 glucose; it had a pH of 7.45±0.02. KHB was gassed with 95% O$_2$, 5% CO$_2$ prior to use.

The electrolyte composition of rat tears was analyzed by atomic absorption spectrometry (Smith Heiftje 22, Thermo Jarrel Ash, Franklin, Mass.). A solution was made to mimic rat tears. The tear buffer contained (mM) 106.5 NaCl, 26.1 NaHCO$_3$, 18.7 KCl, 1.0 MgCl$_2$, 1.1 CaClO$_2$, 0.5 NaH$_2$PO$_4$ and 10.0 HEPES; it had a pH of 7.45±0.02.

Tear buffer was used in which KCl was increased and NaCl decreased (maintaining isotonicity about 330 mOsm/L) to determine the effect of varying the potassium concentration; it had a pH of 7.45±0.02. This tear buffer was gassed with 95% O$_2$, 5% CO$_2$ prior to use.

Statistical Analysis

Data are expressed as mean±SE. Statistical significance was determined by Student's t test for paired and unpaired data.

RESULTS

Figure 3A:
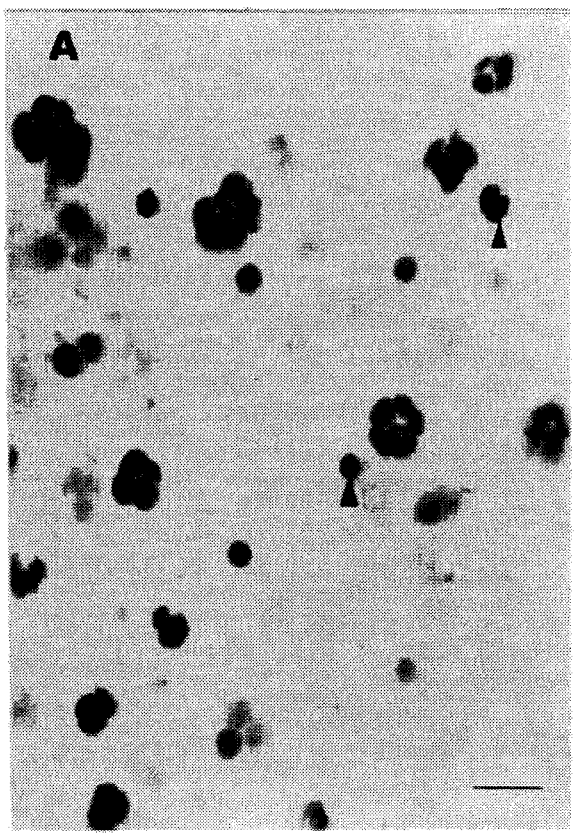
FIGS. 3A and 3B are light microscopy images showing mucin-stained goblet cells in conjunctival buttons removed from superior (3A) and inferior (3B) bulbar conjunctiva of an untreated (control) eye.
Figure 3B:
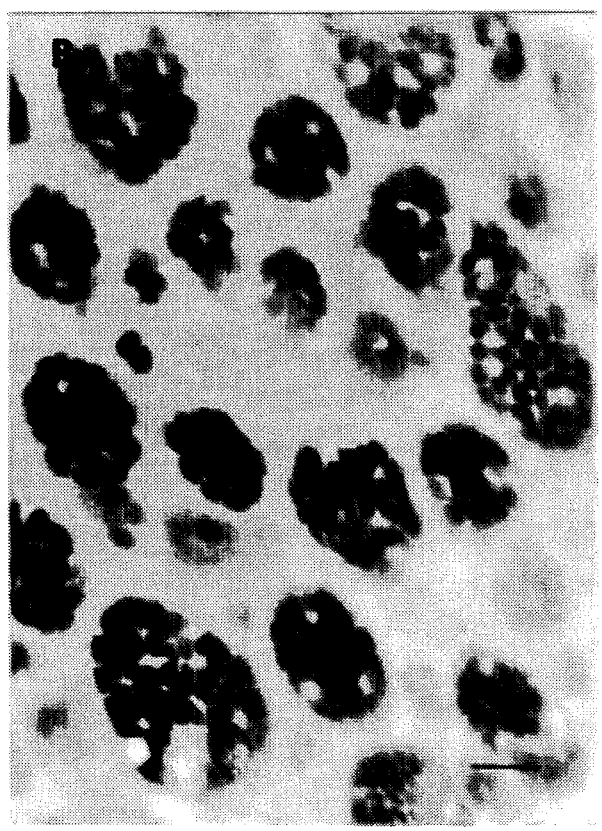
Figure 4A:
FIGS. 4A–4D are light microscopy images showing mucin-stained goblet cells in inferior bulbar conjunctiva: 4A—buffer treated control for FIG. 4B, 4B—dmPGE$_2$ treated (100 μM), 4C—buffer treated control for FIG. 4D, 4D—epinephrine treated (100 μM)
Figure 4B:
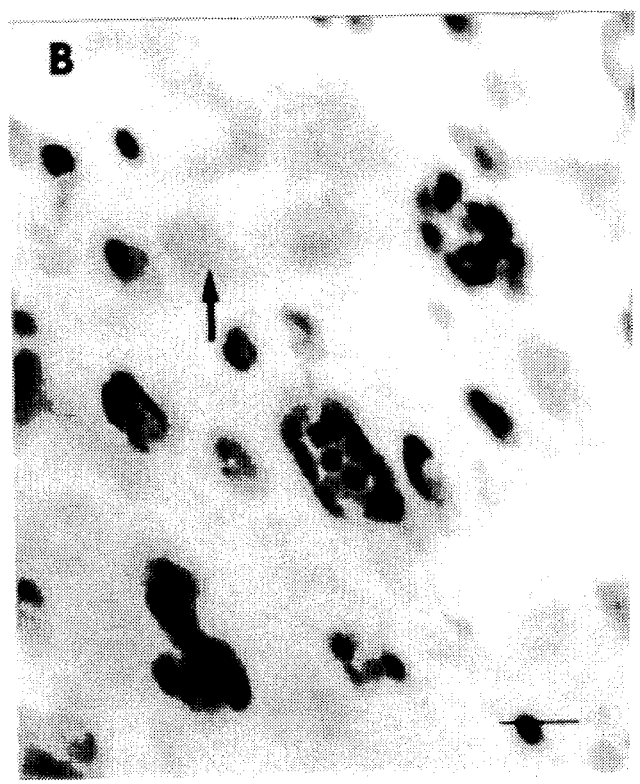
Figure 4C:
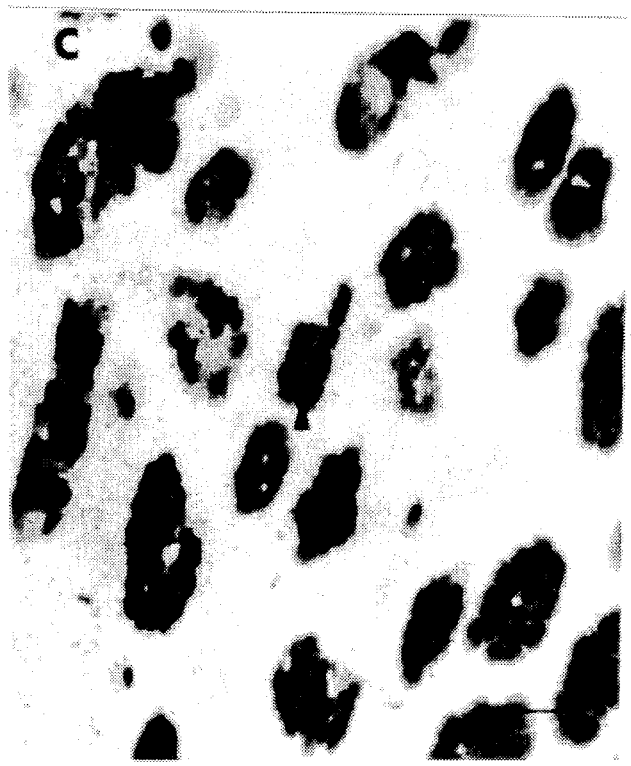
Figure 4D:

Referring to FIGS. 3A and 3B, light micrographs showing mucin-stained goblet cells in conjunctival buttons removed from superior (3A) and inferior (3B) bulbar conjunctiva of a sacrificed, untreated (control) rat eye revealed that superior and inferior bulbar conjunctiva had clusters of variable numbers of mucin-containing goblet cells. The goblet cells had well-defined cell borders and were moderately to intensely stained. (Original magnification ×304; bar=33 μm). It was these intensely stained, well-defined cells that were considered non-secreted and therefore counted (arrowheads in FIG. 3A and 3B). The superior conjunctiva had a lower density of mucin-containing goblet cells than did the inferior conjunctiva.

In untreated control rats, the density of mucin-containing goblet cells of superior conjunctiva of the right eye was 146±14 cells/0.16 mm$^2$ (n=7) and did not differ significantly from that of the left eye with 128±11 cells/0.16 mm$^2$ (n=8). The analogous counts for the inferior conjunctiva were 275±21 cells (n=10) and 270±20 cells (n=8) (difference not significant), respectively. The density of mucin-containing goblet cells did differ significantly (p<0.0001) between inferior and superior conjunctiva; the density ratio was approximately 2:1, respectively.

In subsequent experiments, results obtained from both eyes were combined, but results from superior and inferior conjunctiva were analyzed separately. There is considerable variability in control goblet cell density between animals; thus controls were included in each experiment. The approximately 2:1 ratio between inferior and superior conjunctiva persisted even if absolute number of goblet cells varied between control animals.

Effect of topical application of Krebs-Henseleit buffer

The effect of KHB, which has a serum-like electrolyte composition, was tested to determine if topical application of solutions can be used to study regulation of conjunctival goblet cell mucous secretion. The superior conjunctiva of anesthetized rats had 128±20 mucin-containing goblet cells/0.16 mm$^2$ (n=9) and in rats treated with topical KHB the density was unchanged at 95±15 cells (n=10) compared with anesthetized rats. In the inferior conjunctiva of anesthetized rats the density was 304±34 mucin-containing goblet cells/0.16 mm$^2$ (n=10) and in rats treated with topical KHB the density was unchanged at 358±30 cells (n=11) compared with anesthetized rats. This result indicated that KHB could be used in topical application as a vehicle for a candidate stimulus of goblet cell mucous secretion.

Effect of topical application of tear-like buffer

The ionic composition of rat tears analyzed by atomic absorption was (mmol/L) 143.1 Na$^+$, 18.7 K$^+$, 1.0 Mg$^{2+}$ and 1.1 Ca$^{2+}$. A tear-like buffer was designed to mimic this ion composition and applied to the ocular surface to determine the effect on goblet cell mucous secretion. The superior conjunctiva of anesthetized control rats had 140±26 mucin-containing goblet cells/0.16 mm$^2$ (n=6). In rats treated with topical tear buffer (18.7 mMK$^+$), the density was unchanged at 81±9 goblet cells/0.16 mm$^2$ (n=6) compared with control rats (different not significant). In the inferior conjunctiva of control rats the density was 354±46 cells (n=6) and of rats treated with topical tear buffer (18.7 mM K$^+$) 244+43 cells (n=4) (difference not significant). This result indicated topical application of the tear-like buffer could also be used as a vehicle to study the effects of added agents on mucous secretion.

Since the potassium concentration of rat tears is higher than that of plasma, the effect of varying [K$^+$] on goblet cell mucous secretion was determined. Sodium concentration was adjusted to maintain isotonicity of each solution. Tear buffer solutions containing 4.0 or 37.4 mM K$^+$ were applied to the ocular surface. Conjunctival goblet cell density in superior conjunctiva was unchanged at 107±8 cells and 78±16 cells (n=6) in rats treated with low (4.0 mM) or high (37.4 mM) K$^+$, respectively compared to control (140±26 cells) rats and was unchanged compared to normal 18.7 Mm K$^+$ (81±9 cells).

In the inferior conjunctiva, goblet cell density was unchanged by treatment with tear buffer containing low (265±23 cells (n=5)), or high (304±48 cells (n=5)) [K$^+$] compared to control rats (354±46 cells (n=6)) and was unchanged compared to normal 18.7 mM K$^+$ (244+43 cells). This suggested that varying the K$^+$ concentration does not significantly effect mucous secretion. To determine the effect of buffer osmolarity, rat tear-like buffer in which Na$^+$ was decreased to 133 mM and HEPES added at 10 mM (330 mOsm) or 30 mM (350 mOsm) was used. Neither 330 mOsm buffer (isotonic to rat tears) or 350 mOsm buffer (hypertonic to rat tears) altered goblet cell secretion in the superior and inferior conjunctiva. Thus, conjunctival goblet cell mucous secretion is also not sensitive to osmolarity.

Effect of topical PGE$_2$ analog, dmPGE$_2$

Topical application of tear-like buffer was then used to determine if the effect of a known stimulator of conjunctival goblet cell mucous secretion in another animal system could be detected using the method developed. The prostaglandins PGE$_2$ and PGD were previously shown to stimulate goblet cell mucous secretion in rabbits (3,82). Therefore, the commercially available, stable PGE$_2$ analog, dmPGE$_2$, was topically applied to the ocular surface and the effect on conjunctival goblet cell mucous secretion determined. Since the density of mucin-containing goblet cells did not differ between right and left eyes, only the right eyes of anesthetized rats were treated, the untreated left eyes served as contralateral controls. Contralateral controls from rats with varying treatment could then be compared to determined if treatment in ipsilateral eye affect the contralateral eye.

In the superior bulbar conjunctiva from tear buffer-treated control eyes, mucin-containing goblet cell density was $39\pm28$ cells/0.16 mm$^2$ (n=3) and was unchanged from contralateral control eyes ($43\pm8$ cells). The contralateral controls from buffer-treated, 1, 10, and 100 µM dmPGE$_2$-treated eyes were unchanged from one another. Neither 100 µM, 10 µM, nor 1 µM dmPGE$_2$ significantly altered the density compared with contralateral control eyes or buffer-treated eyes.

In inferior bulbar conjunctiva, tear buffer-treated control eyes had $59\pm18$ mucin-containing goblet cells/0.16 mm$^2$ (n=4), results which were unchanged from contralateral control eyes ($71\pm15$ cells). The contralateral controls from buffer-treated, 1, 10, and 100 µM dmPGE$_2$-treated eyes were unchanged from one another. The cell density in eyes treated with 1 µM and 10 µM dmPGE$_2$ did not differ significantly from control values, but 100 µM dmPGE$_2$ significantly decreased the density to $36\pm12$ goblet cells/0.16 mm$^2$ (n=4) ($P<0.04$) from the value in contralateral control eyes ($75\pm11$ cells/0.16 mm$_2$). 100 µM dmPGE$_2$ decreased the mucin-containing goblet cell density by 30% from the buffer-treated eyes but maintained the 2:1 density ratio between inferior and superior conjunctiva.

Figure 5A:
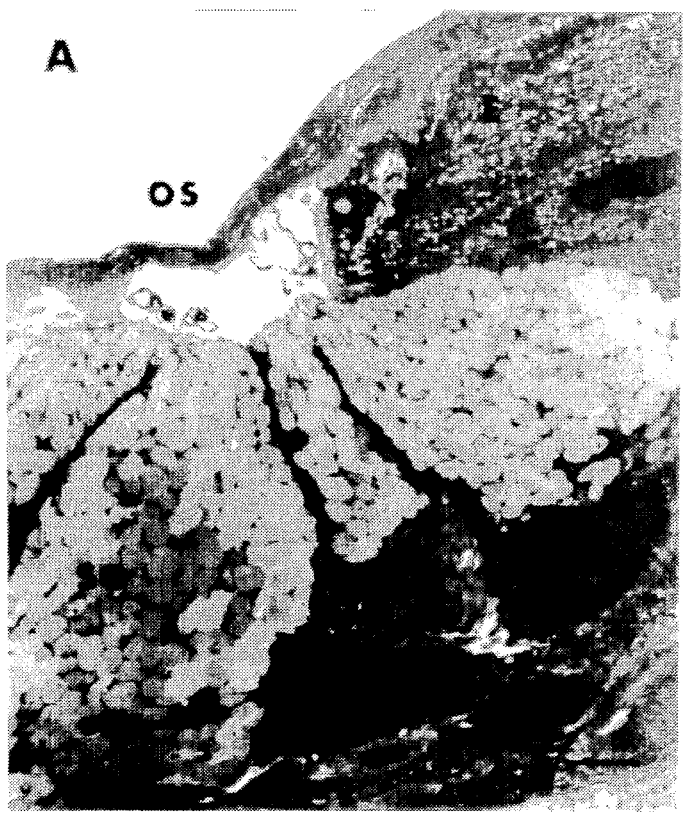
FIGS. 5A–5D are electron micrographs showing mucin-stained goblet cells in inferior bulbar conjunctiva: 5A—buffer treated control for FIG. 5B, and 5B—dmPGE$_2$ treated (600 μM); original magnification ×3,600; bar=3 μM; 5C—buffer treated control for FIG. 5D, and 5D—epinephrine treated (1 μM); original magnification ×2,400; bar=4 μM; OS=ocular surface, N=nucleus, SG=secretory granule, E=epithelial cell.
Figure 5B:
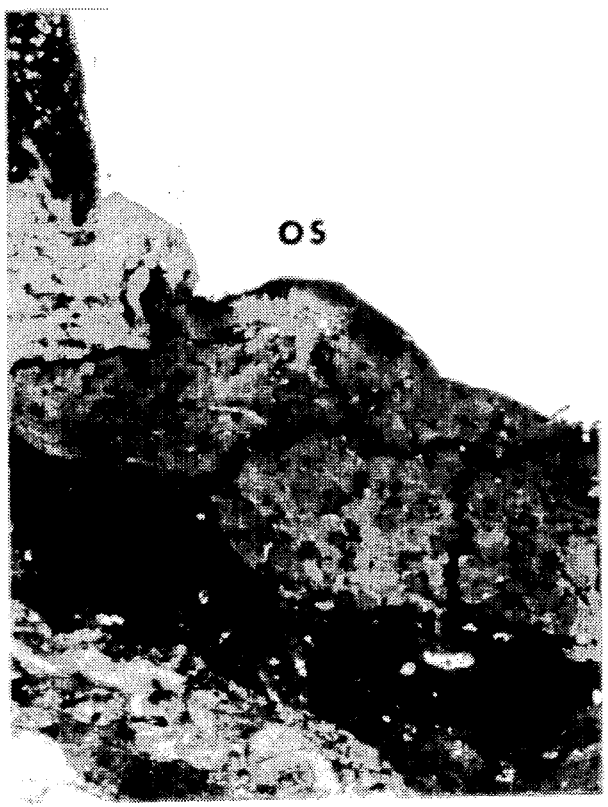

Referring to FIGS. 4A–4D, light microscopy revealed that the mucin-containing goblet cell density in inferior bulbar conjunctiva was decreased with 100 µM dmPGE$_2$ treatment (FIG. 4B) compared with the buffer treated eye (FIG. 4A) or the contralateral control. With dmPGE$_2$ application, fewer stained cells were visible, cells were fuzzy in appearance and released mucus appeared in strands across the conjunctiva. Electron microscopy revealed a goblet cell cluster (FIG. 5A). In the buffer treated eye (FIG. 5A) or contralateral control eye, the goblet cells contained numerous mucous granules. With dmPGE$_2$ stimulation, the goblet cells secreted mucous onto the ocular surface and appeared to be reduced in cell volume with few, if any, intact granules remaining (FIG. 5B).

Effect of topical epinephrine since no changes were observed in superior conjunctiva with dmPGE$_2$ treatment, only the inferior conjunctiva was examined with epinephrine treatment. Tear buffer containing $10^{-8}$, $10^{-6}$, $10^{-4}$M or zero epinephrine was topically applied to the ocular surface of one eye for 1 hr to determine the effect of the adrenergic agonist on goblet cell mucous secretion. The contralateral eye was untreated to determine the effect of the ipsilateral eye on the contralateral eye. There was no significant difference between the contralateral control eyes. Conjunctival goblet cell density in inferior conjunctiva was $257\pm16$ mucin-containing goblet cells/0.16 mm$^2$ (n=5) in the buffer-treated rats and was unchanged at $180\pm55$ cells (n=4) and $200\pm33$ cells (n=6) in rats treated with $10^{-8}$ and $10^{-6}$M epinephrine, respectively. The mucin-containing goblet cell density was significantly ($P<0.04$) decreased to $159\pm35$ cells (n=4) in rats treated with $10^{-4}$M epinephrine.

Figure 5C:
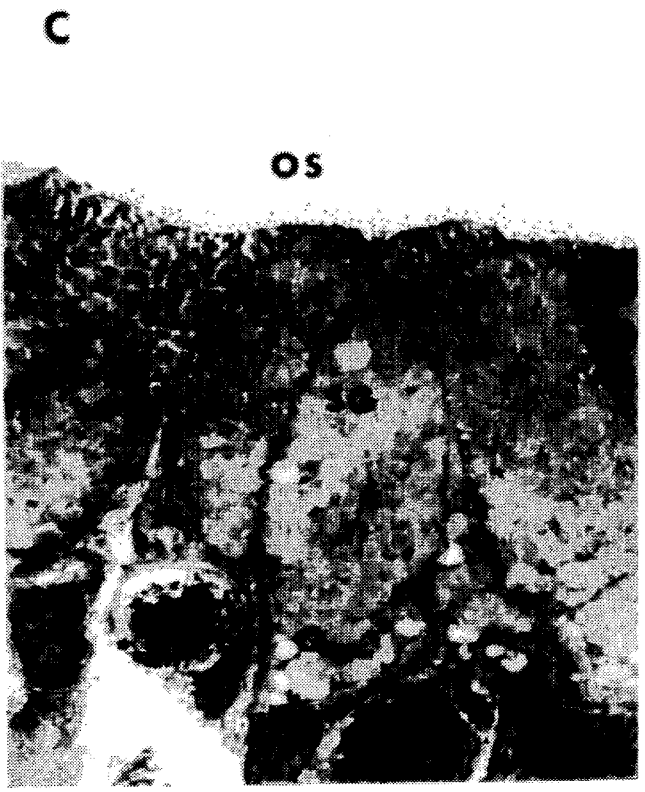
Figure 5D:
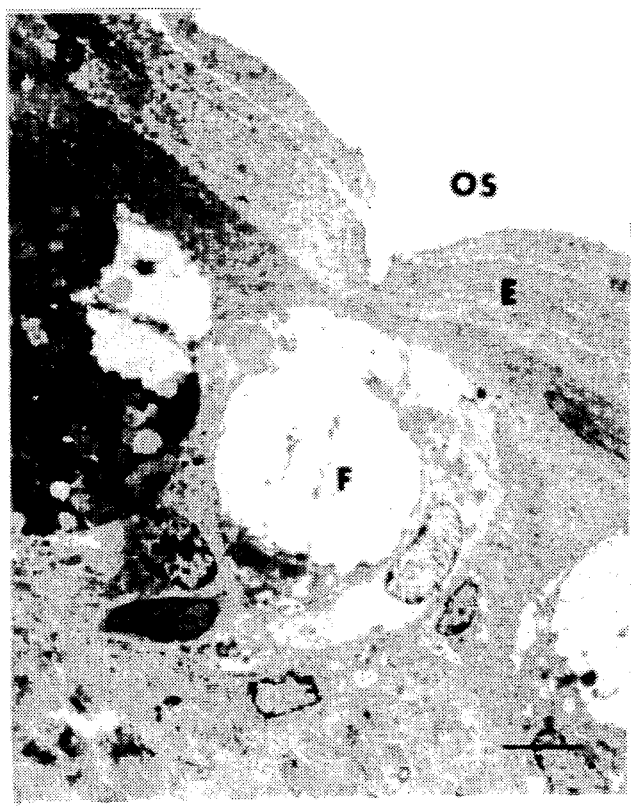

Light microscopy revealed that the mucin-containing goblet cell density in inferior bulbar conjunctiva was decreased with 100 µM epinephrine treatment (FIG. 4D) compared with the buffer treated eye (FIG. 4C) or the contralateral control. With epinephrine application, fewer stained cells were visible and cells were fuzzy in appearance. Electron microscopy revealed a goblet cell cluster (FIG. 5C). In buffer treated eyes (FIG. 5C) and in untreated control eyes, the goblet cells contained numerous mucous granules. With 1 µM epinephrine, some of the goblet cells secreted mucus onto the ocular surface in an all or none fashion and appeared to be reduced in cell volume with few, if any, intact granules remaining (FIG. 5D).

DISCUSSION

When one develops an in vivo rat model for conjunctival goblet cell mucous secretion, several important variables must be controlled. First, the rat goblet cell density varies over the conjunctival surface. In rat, the density of goblet cells is highest in the forniceal zone and decreases toward the limbal and tarsal zones (26). The density also varies from the nasal to the temporal regions with the density highest in the nasal region and decreasing slightly toward the temporal region. The goblet cell distribution in rat (26) is similar to that in humans (30), guinea pigs (38,39), dogs (48), and rabbits (25). Care must be taken to study goblet cell secretion from a consistent location because of the variability of goblet cell density over the conjunctival surface. In the model we have developed, samples are taken from the central bulbar conjunctiva, where there is intermediate goblet cell density.

Second, goblet cell density varies among individuals and among groups of animals. To minimize the effect of this variability in individuals and in groups, proper controls are necessary. Additionally, variability can be minimized by using one eye of each animal as a contralateral control, because (as we have determined) the density of goblet cells does not differ between the right and left eyes.

In the development of the in vivo rat model, mucous secretion was determined by the difference in mucin-containing goblet cell density between stimulated and unstimulated tissue. Goblet cells were identified by histochemical staining of mucins contained in the secretory granules. Goblet cells that contained most of their mucin-containing secretory granules were detected, considered as non-secreted and were counted. Goblet cells that had secreted most or all their mucins were not detected, were considered as secreted and were not counted. Thus, a decrease in density of mucin-containing goblet cells indicated an increase in goblet cell mucous secretion. However, this methodology does not discriminate between complete secretion of mucus and depletion (loss) of the goblet cells. Since the experiments were of only 1-hr duration, loss of entire goblet cells and replacement by newly differentiated cells was not likely to have occurred. Therefore, differentiation of new goblet cells should not have affected the results. The methodology used detected secretion in all-or-none fashion and does not discriminate between partial and no secretion. Small changes in secretion, such as reported with cholinergic agonist stimulation of rat intestinal villus goblet cells, would not be detected (51,55). This partial secretion has not been observed in tracheal goblet cells. Since partial secretion of mucus granules from a given cell cannot be detected by the present methodology, the results could be an underestimate of secretion, missing small effects of agonists. However, the effect of stimuli of goblet cell secretion, such as dmPGE$_2$ and epinephrine, were detected.

The electrolyte composition of tears is different from that of plasma. The [K$^+$] in tears is more than four times higher than the level in plasma, suggesting an active transport of potassium into tears by the lacrimal glands and/or the corneal and conjunctival epithelium. The [Na$^+$] in tears is comparable to plasma levels. Therefore, we determined the short-term effect of varying the tear [K$^+$] on conjunctival goblet cell mucous secretion. Varying the tear [K$^+$] to less than or higher than that in tears did not cause conjunctival goblet cell mucous secretion, suggesting that secretion is not responsive to short-term changes in tear [K$^+$].

There were several differences between the goblet cells in superior and inferior conjunctiva. First, density of mucin-containing goblet cells was less in the superior than the inferior conjunctiva. Second, the mucin-containing goblet cell density was unchanged with dmPGE$_2$ in the superior conjunctiva but was decreased in the inferior conjunctiva with dmPGE$_2$ treatment. There are several possible explanations for these differences. First, differences in the anatomy of the lower lid compared to the upper lid and differences in blinking between these lids could affect conjunctival mucin-containing goblet cell distribution. In the meantime, the density of goblet cells is fairly consistent in the crypt, from duodenum to rectum, but the density in the villi increases from duodenum to distal ileum and continues to increase from the cecum to the rectum (70). Second, the prone placement of the rats in the present experiments could alter the penetration of compounds to the upper and lower conjunctiva. There may be less penetration in the superior than the inferior conjunctiva due to gravity. Third, regulation of goblet cell mucous secretion could differ between the upper and lower conjunctiva. Throughout the small and large intestine, crypt goblet cells are responsive to cholinergic agents but goblet cells on the villus surface are not (51). Finally, since the superior conjunctiva has a lower goblet cell density than inferior conjunctiva, showing a significant decrease in superior conjunctiva was more difficult. The variability among individuals compounded this difficulty. None of these explanations can be eliminated; thus, data from the two conjunctival sites should not be combined.

It has been shown that a PGE$_2$ analog, FCE20700, applied topically can stimulate conjunctival goblet cell mucous secretion in rabbits by morphological detection (3). In that study, Aragona et al. observed mucous secretion from 86.9% and 90.3% of the goblet cells after treatment with FCE20700 (100 μg) for 0.5 hr and 2.5 hr, respectively. A commercially available analog was used to determine if the present methodology was able to detect mucous secretion. We were able to detect a significant decrease (39%) in the mucin-containing goblet cell density with 100 μM (0.8 μg) dmPGE$_2$ in 1 hr compared to buffer-treated eyes. The contralateral control eyes of dmPGE$_2$ treatment (1–100 μM) were unchanged from contralateral control eyes of buffer treatment in both superior and inferior conjunctiva. This indicated that topical application of the prostaglandin analog only stimulated secretion in the eye (inferior conjunctiva) that was treated and does not stimulate secretion in the other eye.

The adrenergic agonist, epinephrine applied topically ($10^{-4}$M) stimulated conjunctival goblet cell mucous secretion compared to buffer-treated eyes. The contralateral control eyes of epinephrine treatment ($10^{-8}$–$10^{-4}$M) were unchanged from contralateral control eyes of buffer treatment. This indicated that topical application of epinephrine only stimulated secretion in the eye that was treated and does not stimulate secretion in the other eye. Unlike conjunctival goblet cells, intestinal goblet cells do not respond to sympathetic agonists (51) but respond to parasympathetic agonists, suggesting conjunctival goblet cell mucous secretion is regulated differently from secretion from goblet cells of other tissues.

We conclude that the in vivo rat model can be used as a model system to test the effects of added agents on conjunctival goblet cell mucous secretion. The similarity in conjunctival goblet cell physiology between rats and humans makes the in vivo rat model a valuable model system for screening candidate therapeutic agents for their effectiveness in treating human patients suffering from aberrant conjunctival goblet cell mucous secretion due to disease or injury.

EXAMPLE II

Sensory stimulation by corneal debridement and topical application of agonists stimulates conjunctival goblet cell mucous secretion.

The experiments in this Example, performed using the rat model system of Example I, show that sensory stimulation by corneal debridement as well as topical application of the additional agents VIP, serotonin, epinephrine, dopamine, phenylephrine, carbachol or Sub P stimulate conjunctival goblet cell mucous secretion.

MATERIALS AND METHODS

Materials

L-phenylephrine hydrochloride, (–)-epinephrine, carbachol (carbamyl choline chloride), 5-hydroxytryptamine (serotonin), and 3-hydroxytyramine (dopamine) were obtained from Sigma (St. Louis, Mo.). Vasoactive Intestinal Peptide (VIP) and Substance P (Sub P) was purchased from Peninsula Laboratories, Inc. (Belmont, Calif.). All other compounds were purchased from Sigma or Fisher (Pittsburgh, Pa.) unless indicated otherwise.

Animals

Male Sprague-Dawley rats at 12 weeks of age (young adults) (Charles River Laboratories, Wilmington, Mass.) were anesthetized with intraperitoneal injection of 65 mg/kg of sodium pentobarbital or anesthetized with intraperitoneal injection of 100 mg/kg ketamine and 6.7 mg/kg acepromazine. All experiments conformed to the USDA Animal Welfare Act (1985) and Schepens Eye Research Institute Animal Care and Use Committee.

Sensory stimulation by corneal debridement

To determine the effect of sensory stimulation by central corneal debridement, rats were anesthetized with pentobarbital. The central cornea of one eye was debrided (2–3 mm diameter area) and 5, 30, 60, or 120 min later the animal was euthanized with intraperitoneal sodium pentobarbital (1300 mg/kg).

Neurotransmitters

To determine the effect of topically applied compounds, an experimental buffer containing the test compound (20 μl drops) was placed on one eye from the temporal region every 20 min for 1 hr unless otherwise indicated. The buffer, designed to mimic tear ionic composition, contained 106.5 mM NaCl, 26.1 mM NaHCO$_3$, 18.7 mM KCl, 1.0 mM MgCl$_2$, 1.1 mM CaCl$_2$, 0.5 mM NaH$_2$PO$_4$, and 10 mM HEPES; it had a pH of 7.45±0.02 and a calculated osmolarity of 330 mOsm/L. The tear buffer for the neurotransmitter dopamine contained 1 mM ascorbic acid. The solutions were removed from the nasal region of the eye with a cotton-tipped applicator. After the 1 hr protocol, animals were euthanized with sodium pentobarbital.

Measurement of Goblet Cell Density

Measurement of goblet cell density and scoring parameters were as in Example I.

RESULTS AND DISCUSSION

Results are expressed as percent of contralateral control. Sixty min after sensory stimulation by corneal debridement, the mucin-containing goblet cell density was significantly decreased by 55% (P<0.05) (n=4–5) to 147±29 mucin-containing goblet cells from contralateral controls at 322±28 cells. The mucin-containing goblet cell density in sham-wounded eyes at 131±21 cells (P<0.006) was unchanged from either its contralateral controls at 156±16 cells or from un-wounded eyes at 183±39 cells.

In a second experiment, the time course of the decrease in mucous secretion following sensory stimulation was examined. Mucin-containing goblet cell density was significantly decreased from contralateral untreated eyes (161±29 cells/0.16 mm$^2$, 213±18, 302±26 and 324±27 cells) to 103±16, 100±11, 129±32 and 136±15 cells (n=4–6) (P<0.02) in rats euthanized at 5, 30, 60, and 120 min after sensory stimulation by corneal debridement, respectively. This indicates that sensory stimulation of mucous secretion can be seen as early as 5 min after corneal debridement and is consistent with a neurally-mediated response.

The stimulation of goblet cell secretion by corneal debridement suggests that ocular damage stimulates the reflex sensory neurons (afferent neurons) of the cornea to activate a local reflex arc. In turn the efferent neurons in the conjunctiva would be activated and at their termini would release neuro-transmitters to stimulate the conjunctival goblet cells, either directly or indirectly.

Various neurotransmitters were then surveyed for their ability to stimulate the same effect as corneal debridement. We first tested VIP because VIP-binding sites were found in rat and rabbit conjunctiva (15) and VIP-like immunoactivity was shown in nerves of rat limbal blood vessels (74). Since sites exist in the conjunctiva for potential VIP action, the effect of topical application of VIP ($10^{-10}$–$10^{-6}$M) on goblet cell secretion was determined. In inferior conjunctiva the maximum effect was obtained with $10^{-8}$M VIP, which significantly decreased the mucin-containing goblet cell density by 39% (P<0.05) (n=5–6) to 150±23 cells from contralateral controls at 243±23 cells. In contrast, goblet cell density in buffer-treated eyes at 197±32 cells was not significantly different from contralateral control eyes at 210±22 cells. This VIP stimulation of mucous secretion in conjunctiva is unlike that of intestinal goblet cells in which VIP does not effect secretion of intestinal goblet cells (51). In most tissues VIP is localized in parasympathetic nerves. Thus, VIP appears to be one of the neurotransmitters of parasympathetic nerves that mediates the efferent arm of the reflex arc that stimulates conjunctival goblet cell secretion.

Serotonin has been identified in the nerves of the cornea (33). Serotonin was shown to enhance phosphoinositol turnover in rabbit cornea and to cause electrolyte and water secretion into the tear film (1). Therefore, serotonin ($10^{-8}$–$10^{-4}$M) was chosen to determine the effect on goblet cell secretion. In inferior conjunctiva the maximum effect was obtained with $10^{-8}$M serotonin which significantly decreased the mucin-containing goblet cell density by 54% to 148±27 cells from contralateral eyes (306±50 cells) (P<0.02) (n=3–4). The buffer-treated eyes were not significantly different from contralateral control eyes. Interestingly, in intestinal goblet cells, unlike in conjunctival goblet cells, serotonin had no effect on mucous secretion (51). However, we have determined that in the conjunctiva, serotonin appears to mediate the efferent arm of the reflex arc to stimulate goblet cell secretion.

Since sympathetic nerves innervate the conjunctiva, the adrenergic neurotransmitters epinephrine ($10^{-8}$–$10^{-4}$M), phenylephrine ($10^{-8}$–$10^{-4}$M) and dopamine ($10^{-8}$–$10^{-4}$M) were each applied to the ocular surface. Epinephrine at $10^{-4}$M, phenylephrine at $10^{-4}$M, and dopamine at $10^{-8}$M each gives the maximum effect. The mucin-containing goblet cell density in inferior conjunctiva treated with $10^{-4}$M epinephrine, $10^{-4}$M phenylephrine, or $10^{-8}$M dopamine was significantly decreased by 46%, 40%, and 64% (P<0.03) (n=3–6), respectively, from contralateral control values. The buffer-treated eyes were not significantly different from contralateral control eyes. The stimulation of mucous secretion in conjunctival goblet cells with epinephrine, phenylephrine, or dopamine was unlike that of intestinal goblet cells where no effect on secretion was observed (51). Also, in contrast to the present study, long term exposure of rabbit ocular surface with the vasoconstrictor, phenylephrine does not significantly affect conjunctival goblet cell density (63). However, Shellans et al. (63) do not report on the short-term effect it has on goblet cell secretion. The results of the present study indicate that sympathetic nerves also mediate the efferent arm of the stimulatory pathway for goblet cell secretion.

In addition, carbachol at $10^{-7}$ and $10^{-6}$M, but not at $10^{-5}$–$10^{-4}$M, decreased mucin-containing goblet cell density. A maximum decrease of 40% (P<0.032) (n=3) was obtained at $10^{-6}$M compared to the contralateral control eye. Thus parasympathetic nerves could stimulate conjunctival goblet cell mucin secretion.

Substance P at $10^{-6}$M, but not at $10^{-10}$ or $10^{-8}$M, decreased mucin-containing goblet cell density (77±18 cells) by 58% (p<0.005) (n=4) compared to the contralateral control eye (188±19 cells). This indicates that sensory nerves could stimulate conjunctival goblet cell mucin secretion.

Table I (below) presents a summary of various nervous system stimuli and inhibitors of conjunctival goblet cell mucous secretion. The listed agonists have been tested as described and the results obtained are reported. The antagonists given are representative examples of an appropriate inhibitor for each specific nerve type and include: the muscarinic, parasympathetic antagonist atropine; the nicotinic, parasympathetic antagonist d-tubocurarine; the α-adrenergic antagonist phentolamine; the $\alpha_1$-adrenergic antagonist prazosin; the $\alpha_2$-adrenergic antagonist yohimbine; the β-adrenergic antagonist timolol; the dopaminergic antagonist haloperidol; the serotonergic antagonist methysergide; the VIP antagonist [4-Cl-D-Phe$^6$,Leu$^{17}$]-VIP and the Sub P antagonist [D-Arg$^1$, D-phe$^5$, D-Trp$^{7,9}$, Leu$^{11}$]-Substance P. The use of other similar compounds is within the method of the invention; a recitation of specific examples is not intended to limit the scope of protection sought.

TABLE 1

Nervous System Stimuli and Inhibitors of Conjunctival Goblet Cell Mucous Secretion

| Stimulus | Inhibitor | Nerve Type | (Stimulus) Optimal Effective Conc. (M) | (Stimulus) Max % Increase in Secretion |
|---|---|---|---|---|
| Corneal Wounding | ? | ? | — | 65 |
| Carbachol | Atropine, d-Tubocurarine | Parasymp. | $10^{-6}$ | 41 |
| Epinephrine | Phentolamine | Sympathetic | $10^{-2}$ | 52 |
| Phenylephrine | Prazosin | Sympathetic | $10^{-4}$ | 40 |
| Clonidine | Yohimbine | Sympathetic | ND | ND |

TABLE 1-continued

Nervous System Stimuli and Inhibitors of Conjunctival Goblet Cell Mucous Secretion

| Stimulus | Inhibitor | Nerve Type | (Stimulus) Optimal Effective Conc. (M) | (Stimulus) Max % Increase in Secretion |
|---|---|---|---|---|
| Isoproterenol | Timolol | Sympathetic | ND | ND |
| Dopamine | Haloperidol | Sympathetic | $10^{-8}$ | 64 |
| Serotonin | Methysergide | CNS Neurons, Endocrine & Mast Cells | $10^{-8}$ | 54 |
| VIP | Synthetic peptide | Parasymp. | $10^{-8}$ | 39 |
| Substance P | Synthetic peptide | Sensory | $10^{-6}$ | 42 |

ND, not done; ?, not known;

EXAMPLE III

Method for Testing the Effectiveness of a Candidate Agent

This method is used for further testing of the effectiveness of a candidate agent that has been shown to be effective using the rat model system. In an exemplary assay, a 50 μl drop of the candidate agent (stimulus, inhibitor and/or both dissolved in a physiologically compatible vehicle at a concentration found to be effective in rats) is placed on the ocular surface of one eye of a human patient, and the same size drop of buffer is applied to the ocular surface of the other eye. In 5–60 min, a 50 μl drop of a 1% solution of lidocaine (a local anesthetic) is placed on the ocular surface of both the treated and contralateral eyes. After an additional wait of 10 min, a conjunctival sample is removed for biopsy or impression cytology. Cells may be stained with Alcian Blue and periodic acid-Schiff's reagents and the number of mucin-containing goblet cells determined. In addition, the sample may be treated with Gill's modified Papanicolaou stain to stain all cells. For a determination of long term effectiveness, the candidate agent may be applied, e.g., 4–6 times/day for 4–12 weeks before lidocaine addition and sample removal.

EXAMPLE IV

The Effects of a Local Anesthetic on Conjunctival Goblet Cell Mucous Secretion

MATERIALS AND METHODS

Materials

Ophthaine (0.5% proparacaine) was purchased from E. R. Squibb & Sons, Inc. (Princeton, N.J.). Proparacaine hydrochloride and lidocaine hydrochloride were obtained from Sigma (St. Louis, Mo.).

Animals

Male Sprague-Dawley rats at 12 weeks of age (young adults) (Charles River Laboratories, Wilmington, Mass.) were anesthetized with intraperitoneal injection of 65 mg/kg of sodium pentobarbital. All experiments conformed to the USDA Animal Welfare Act (1985) and Schepens Eye Research Institute Animal Care and Use Committee.

Administration of local anesthetics

Rats were anesthetized with sodium pentobarbital (65 mg/kg). To determine the effect of topical application of local anesthetics, a buffer designed to mimic tear ionic composition (see EXAMPLE II) and containing a test compound (20 μl drops) was placed on one eye from the temporal region once, 15 min before corneal debridement. To determine the effect of subconjunctval injection of these compounds, a buffer designed to mimic serum ((mM) 115.0 NaCl, 25.0 NaHCO$_3$, 4.0 KCl, 1.0 MgCl$_2$, 0.5 NaH$_2$PO$_4$ and 1.1 CaCl$_2$; pH 7.45±0.02) and containing the test compound (30 μl) was injected subconjunctivally into the superior nasal region once before corneal debridement.

Sensory stimulation by corneal debridement

Fifteen min after application of local anesthetic, the central cornea of one eye was wounded by debridement (2–3 mm diameter area), the other was sham-debrided and 5 min later the animal was euthanized with intraperitoneal sodium pentobarbital (1300 mg/kg).

Measurement of goblet cell density

Measurement of goblet cell density and scoring parameters were as in Example I.

RESULTS AND DISCUSSION

Effect of topically administered 0.5% proparacaine on sensory stimulation

Proparacaine was topically applied to determine the effect of this local anesthetic on sensory stimulation of mucous secretion. The local anesthetics, commercial 0.5% proparacaine (Ophthaine from Squibb) and 0.5% proparacaine in tear buffer were unable to inhibit sensory stimulation of mucous secretion. This suggested that either the anesthetic did not penetrate the ocular surface to block nerve action or that the anesthesia was not strong enough to block the sensory stimulation of mucous secretion. A more potent anesthesia (1% lidocaine) was chosen to determine the effect it has on sensory stimulation of goblet cell mucous secretion.

Effect of topical and sub-conjunctival injection of 1% lidocaine

Lidocaine (1%) in tear buffer was topically applied and a 1% lidocaine in serum buffer was sub-conjunctivally injected to determine the effect of dual-site lidocaine on sensory stimulation mucous secretion. Goblet cell density was significantly decreased (44%) from contralateral sham-wounded eyes (147±11 mucin-containing goblet cells/0.16 mm$^2$) to 85±18 cells (n=6) (P<0.016) in wounded eyes. The number of mucin-containing goblet cells in eyes treated with topical and sub-conjunctival injection of 1% lidocaine and then wounded (132±21 cells) was unchanged compared to contralateral sham-wounded eyes with similar lidocaine treatment (110±25 cells). The mucin containing goblet cell density in eyes treated with both topical tear buffer and sub-conjunctival injection of serum buffer was unchanged from contralateral untreated eyes. In un-wounded eyes, the mucin-containing goblet cell density in eyes treated with both topical 1% lidocaine in tear buffer and sub-conjunctival injection of 1% lidocaine in serum buffer was unchanged from un-wounded, contralateral eyes with respective treatments of tear and serum buffers alone. This indicated that topical and sub-conjunctival injection of lidocaine inhibited the sensory stimulation of goblet cell mucous secretion. We concluded that the sensory stimulation was neurally mediated and that neural stimulation causes conjunctival goblet cell mucous secretion.

Effect of topically applied 1% lidocaine

Since the combination of both topical and sub-conjunctival injection of lidocaine inhibited sensory stimulation of mucous secretion, topical lidocaine alone and sub-conjunctival injection of lidocaine alone were performed to determine the effect of single-site lidocaine on sensory stimulation of mucous secretion. Mucin-containing goblet cell density was significantly decreased (61%) in wounded eyes ($31\pm6$ cells/$0.16$ mm$^2$ (n=4) (P<0.0014)) compared to $86\pm8$ cells in contralateral sham-wounded eyes. The number of mucin-containing goblet cells in eyes treated with topical 1% lidocaine prior to the wound ($84\pm7$ cells) was unchanged from sham-wounded eyes treated with lidocaine ($78\pm5$ cells (n=4)). As a control, the mucin-containing goblet cell density in un-wounded eyes treated with tear buffer was unchanged compared to un-wounded contralateral untreated eyes. As a control, the density in un-wounded eyes treated with topical 1% lidocaine in tear buffer was unchanged from un-wounded eyes treated with tear buffer alone. This indicated that topical lidocaine inhibited sensory stimulation of mucous secretion.

Effect of sub-conjunctival injection of 1% lidocaine

Sub-conjunctival injection of 1% lidocaine was performed to determine the effect of applying the local anesthetic in proximity to the nerves stimulating mucous secretion. Goblet cell density was significantly decreased (40%) in wounded eyes ($42\pm8$ cells/$0.16$ mm$^2$ (n=4) (P<0.021)) compared to $72\pm6$ cells in sham-wounded eyes. The number of mucin-containing goblet cells in eyes treated with sub-conjunctival injection of 1% lidocaine prior to the wound ($100\pm28$ cells) was unchanged from $98\pm24$ cells in contralateral sham-wounded eyes with lidocaine injection. As a control, the mucin-containing goblet cell density in un-wounded eyes treated with sub-conjunctival injection of serum buffer was unchanged from un-wounded contralateral untreated eyes. As a control, sub-conjunctival injection of 1% lidocaine in serum buffer into un-wounded, eyes did not change the density compared to un-wounded contralateral eyes treated with serum buffer alone. This indicated that sub-conjunctival injection of lidocaine inhibited sensory stimulation of mucous secretion.

Conclusion

We conclude from these experiments that sensory stimulation by corneal debridement is neurally mediated and that neural stimulation causes conjunctival goblet cell mucous secretion. The neural stimulation can be blocked by use of certain local anesthetics. Thus, neural stimulation could be mimicked by application of compounds that activate nerves or have actions similar to neurotransmitters. Our results provide further evidence that stimulation of nerves causes conjunctival goblet cell mucous secretion and inhibition of nerves prevents it. Thus, topical application of a local anesthetic could be used to prevent a change in conjunctival goblet cell mucous secretion in cells removed from humans and allow diagnosis of human patients suffering from aberrant conjunctival goblet cell mucous secretion due to disease or injury.

EXAMPLE V

Innervation of Goblet Cells

The experiments in this Example, performed using the rat model system of EXAMPLE I, show that conjunctival goblet cells are directly innervated and that topical application of lidocaine or other local anesthetics prevents conjunctival goblet cell mucous secretion so that the unsecreted goblet cells can be removed and studied.

MATERIALS AND METHODS

Materials

Lidocaine hydrochloride was purchased from Sigma Chemical Company (St. Louis, Mo.). A monoclonal antibody to synaptophysin was purchased from Boehringer Mannheim Biochemica (Indianapolis, Ind.). A polyclonal antibody to VIP was purchased from Amersham International (Arlington Heights, Ill.). The secondary antibodies used were donkey-anti-rabbit IgG conjugated to fluorescein isothiocyanate (FITC) and donkey-anti-mouse IgG conjugated to FITC. Both were purchased from Jackson Immunoresearch Laboratories Inc. (West Grove, Pa.).

Animals

Male Sprague-Dawley rats at 12 weeks of age (young adults) (Charles River Laboratories, Wilmington, Mass.) were sacrificed with intraperitoneal injection of 1300 mg/kg of sodium pentobarbital.

Preparation of tissue

Rats were either untreated or a 20 µl drop of 1% lidocaine dissolved in tear buffer was placed on the ocular surface of both eyes for 5 min or 10 min. The globe of the eye was excised. The posterior half of the globe was removed, followed by removal of the lens and iris. The remaining tissue (the ocular surface) including the cornea, the limbus, and the bulbar conjunctiva was frozen in O. C. T. Compound (Miles Inc., Elkart, Ind.).

Light microscopy

Tissue sections (20 µm) were prepared from the ocular surface and stained with hematoxylin and eosin (H and E). Sections were examined using an Olympus Microscope (BH-2; Micro-Tech Optical, Inc., Hudson, Mass.).

Immunofluorescence microscopy

Cryostat sections (20 µm) were placed on gelatin-coated slides, air-dried for 1–2 hrs at room temperature, rehydrated in phosphate buffered saline (PBS), and blocked in 1% BSA dissolved in PBS for 10 min.

Monoclonal antibody for synaptophysin (1:10) or polyclonal antibody to VIP (1:500) was applied and incubated for 1 hr. The slides were rinsed for 10 min in 1% BSA-PBS and incubated with secondary antibody (1:50) for 1 hr. The sections were viewed and photographed using a Zeiss Axiophot (Thornwood, N.Y.) with an epi-illumination system. To assess immunohistochemical specificity, tissue sections were incubated with the FITC-conjugated secondary antiserum alone.

RESULTS AND DISCUSSION

Figure 6A:
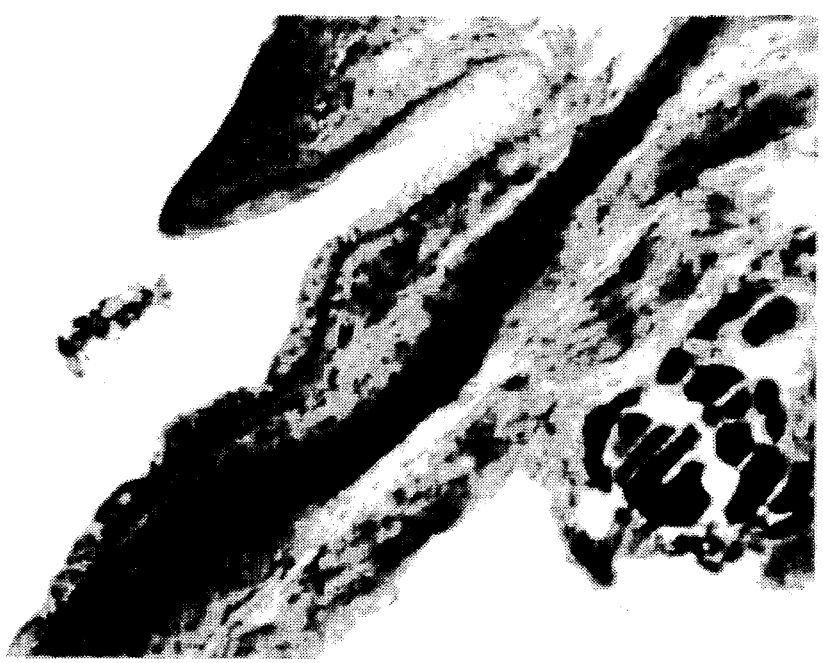
FIGS. 6A–6C are light microscopy images showing goblet cells in inferior bulbar conjunctiva; 6A—untreated, 6B—5 min lidocaine (1%)-treated, 6C—10 min lidocaine (1%)-treated.

Goblet cells were identified morphologically in H- and E-stained sections. In conjunctiva without lidocaine treatment, only an occasional goblet cell was detected (FIG. 6A).

Figure 6B:
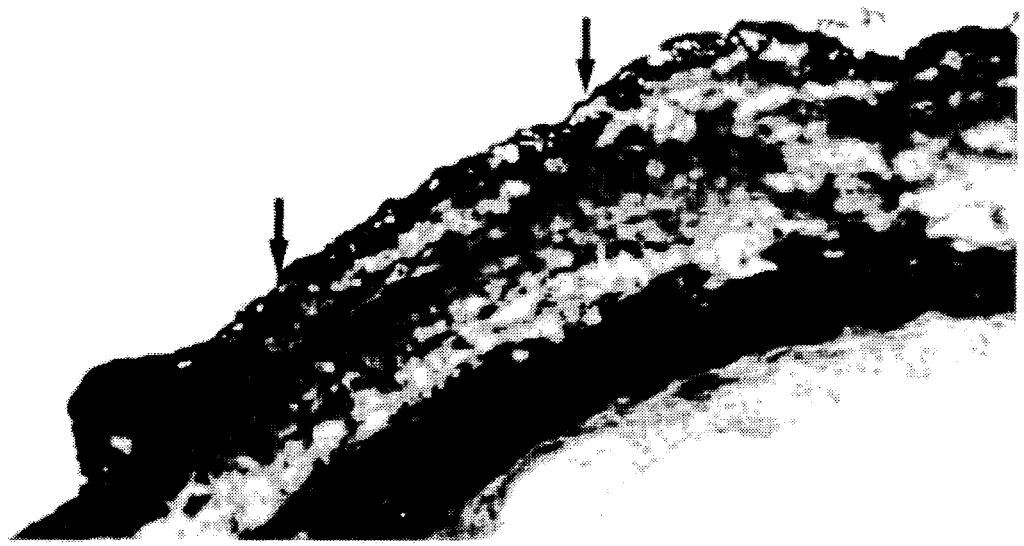
Figure 6C:

In conjunctiva treated with lidocaine for 5 min some goblet cells (indicated by arrows) were detected (FIG. 6B). In conjunctiva treated with lidocaine for 10 min numerous goblet cells (indicated by arrows) were present (FIG. 6C). This suggests that lidocaine prevents goblet cells from secreting and preserves them for subsequent histochemical analysis.

Untreated conjunctiva or conjunctiva treated for 10 min with lidocaine were examined for synaptophysin-like immunoreactivity (S-LI) and VIP-like immunoreactivity (VIP-LI). Synaptophysin is a protein found in nerve terminals in general, independent of the type of nerve. Presence of synaptophysin does not distinguish between sensory, parasympathetic or sympathetic nerves but does indicate the presence of nerves. S-LI and VIP-LI nerve fibers were detected in all lidocaine-treated conjunctiva examined and had the typical varicose appearance and meandering course of terminal nerve fibers. S-LI and VIP-LI nerve fibers had a similar pattern. Control experiments confirmed the specificity of the immunohistochemical reaction, as use of FITC-conjugated antiserum alone failed to stain conjunctival nerve fibers.

Figure 7A:
FIGS. 7A–7B are fluorescence microscopy images of nerves in the inferior bulbar conjunctiva treated with lidocaine (1%) for 10 min and indicate: 7A—synaptophysin-like immunoreactivity and 7B—VIP-like immunoreactivity.
Figure 7B:

Goblet cells in lidocaine-treated conjunctiva were identified as the dark regions of the epithelium (hazy white area) in immunofluorescence microscopy and were identified structurally by phase contrast microscopy. S-LI and VIP-LI nerve fibers (indicated by arrows) were present around the basal, but not the apical, portion of goblet cells in lidocaine-treated conjunctiva (FIG. 7A and 7B). S-LI and VIP-LI nerve fibers were not detected around goblet cells in untreated sections because of the greatly reduced number of goblet cells.

We conclude that a 10 min treatment with lidocaine (one 20 μl drop of 1% lidocaine) prevents goblet cell mucous secretion and allows visualization of substantial numbers of goblet cells in conjunctival sections. Our results demonstrate that similar application of local anesthetic could be used to remove conjunctival goblet cells from humans to allow diagnosis of human patients suffering from aberrant conjunctival goblet cell mucous secretion due to disease or injury. We conclude that S-LI and VIP-LI nerves are present around goblet cells. This result suggests that goblet cells are innervated and that parasympathetic nerves are probably present as VIP usually coexists with acetylcholine, the postganglionic parasympathetic neurotransmitter. It also suggests that sensory stimulation by corneal debridement and topical application of neurotransmitters stimulates directly conjunctival goblet cell mucous secretion. Finally, our results provide additional evidence that topical application of neural stimuli can cause conjunctival goblet cell mucous secretion and that neural inhibitors can block it.

REFERENCES

1. Akhtar R. A. Effects of norepinephrine and 5-hydroxytryptamine on phosphoinositide-$PO_4$ turnover in rabbit cornea. Exp. Eye Res. 44:849–862, 1987.
2. Allansmith M. R., Baird R. S., Greiner J. V. Density of goblet cells in vernal conjunctivitis and contact lens-associated giant papillary conjunctivitis. Arch. Ophthalmol. 99:884–885, 1981.
3. Aragona P., Candela V., Caputi A. P., Micali A., Puzzolo D., Quintieri M. Effects of a stable analogue of $PGE_2$ (11-deoxy- 13,14-didehydro-16(S)-methylester methyl $PGE_2$: FCE 20700) on the secretory processes of conjunctival goblet cells of rabbit. Exp. Eye Res. 45:647–654, 1987.
4. Augeron C., Voisin T., Maoret J. J., Berthon B., Laburthe M., Laboisse C. L. Neurotensin and neuromedin N stimulate mucin output from human goblet cells (Cl. 16E) via neurotensin receptors. Am. J. Physiol. 262:G470–G476, 1992.
5. Barnes P. J., Chung K. F., Page C. P. Inflammatory mediators and asthma. Pharm. Rev. 40:49–84, 1988.
6. Basbaum C. B., Jany B., Finkbeiner W. E. The serous cell. Ann. Rev. Physiol. 52:97–144, 1990.
7. Braga P. C., Ziment I., Allegra L. Classification of agents that act on bronchial mucus. In: Drugs and Bronchial Mucology; edited by P. C. Braga and L. Allegra, New York: Raven Press, pp. 59–67, 1989.
8. Butler J. M., Ruskell G. L., Cole D. F., Unger W. G., Zhang S. Q., Blank M. A., McGregor G. P., Bloom R. Effects of VIIth (facial) nerve degeneration on vasoactive intestinal polypeptide and substance P levels in ocular and orbital tissues of the rabbit. Exp. Eye Res. 39:523–532, 1984.
9. Carlstedt I., Sheehan J. K., Corfield A. P., Gallagher J. T. Mucous glycoproteins: A gel of a problem. Essays Biochem. 20:40–76, 1985.
10. Carraway K. L., Hull S. R. O-glycosylation pathway for mucin-type glycoproteins. Bioessays 10:117–121, 1989.
11. Chao C. W., Brown S. I. Macromolecular components of human ocular mucus. In: the Preocular Tear Film in Health, Disease and Contact Lens Wear; edited by F. J. Holly. Lubbock Tex.: Dry Eye Institute; pp. 331–340, 1986.
12. Chao C. W., Butala S. M., Herp A. Studies on the isolation and composition of human ocular mucin. Exp. Eye Res. 47:185–196, 1988.
13. Dartt D. A., Smith D. M. Stimulation of Rat Conjunctival Goblet Cell Mucus Secretion. ARVO Abstracts. Invest. Ophthalmol. Vis. Sci. 31(Suppl):408, 1990.
14. Davis C. W., Dowell M. L., Lethem M., VanScott M. Goblet cell degranulation in isolated canine tracheal epithelium: response to exogenous ATP, ADP, and adenosine. Am. J. Physiol. 262:C1313–C1323, 1992.
15. Denis P., Dussaillant M., Nordmann J., Elena P., Sarauy H., Rostene W. Autoradiographic characterization and localization of vasoactive intestinal peptide binding sites in albino rat and rabbit eyes. Exp. Eye Res. 52:357–366, 1991.
16. Dohlman C. H., Friend J., Kalerar V., Yagoda D., Balazs E. The glycoprotein (mucus) content of tears from normals and dry eye patients. Exp. Eye Res. 22:359–365, 1976.
17. Friend J., Kiorpes T., Thoft R. A. Conjunctival goblet cell frequency after alkali injury is not accurately reflected by aqueous tear mucin content. Invest. Ophthalmol. Vis. Sci. 24:612–618, 1983.
18. Geggel H. S., Gipson I. K. Removal of viable sheets of conjunctival epithelium with Dispase II. Invest. Ophthalmol. Vis. Sci. 26:15–22, 1985.
19. Gipson I. K., Yankaucas M. Spurr-Michaud S. J., Tisdale A. S., Rinehart W. Characteristics of a glycoprotein in the ocular surface glycocalyx. Invest. Ophthalmol. Vis. Scio 33:218–227, 1992.
20. Greiner J. V., Henriquez A. S., Covington H. I., Weidman T. A., Allansmith M. R. Goblet cells of the human conjunctiva. Arch. Ophthalmol. 99:2190–2197, 1981.

21. Greiner J. V., Weidman T. A., Korb D. R., Allansmith M. R. Histochemical analysis of secretory vesicles in nongoblet conjunctival epithelial cells. Acta Ophthalmol. 63:89–92, 1985.

22. Hoffstein S. T., Malo P. E., Bugelski P., Wheeldon E. B. Leukotriene $D_4$ ($LTD_4$) induces mucus secretion from goblet cells in the guinea pig respiratory epithelium. Exp. Lung Res. 16:711–725, 1990.

23. Holly F. J., Lemp M. A. Tear physiology and dry eyes. Ophthalmol. 22:69–87, 1977.

24. Holtzman M. J. Arachidonic acid metabolism in airway epithelial cells. Annu. Rev. Physiol. 54:303–329, 1992.

25. Huang A. J. W., Tseng S. C., Green W. R. Distribution of conjunctival goblet cells in normal rabbits. Invest. Ophthalmol. Vis. Sci. 25 (Suppl):322, 1984.

26. Huang A. J. W., Tseng S. C. G., Kenyon K. R. Morphogenesis of rat conjunctival goblet cells. Invest. Ophthalmol. Vis. Sci. 29:969–975, 1988.

27. Jensen O. A., Falbe-Hansen I., Jacobsen T., Michelsen A. Mucosubstances of the acini of the human lacrimal gland (orbital part). I. Histochemical identification. Acta Ophthalmol. 47:605–619, 1969.

28. Jumblatt M. M., Schack B. W., and Jumblatt J. E. Intracellular Mediators of Conjunctival Mucin Secretion. ARVO Abstracts. Invest. Ophthalmol. Vis. Sci. 34(Suppl):822, 1993.

29. Karjalainen K., Tervot, Palkama A. Catecholamine-containing and acetyl cholinesterase-positive nerve fibers in the rabbit conjunctiva. Acta Ophthalmol. 56:911–920, 1978.

30. Kessing S. V. Mucous gland system of the conjunctiva. Acta Ophthalmol. 46(Suppl 95):9–133, 1968.

31. Kim K. C., Lee B. C. $P_2$ purinoceptor regulation of mucin release by airway goblet cells in primary culture. Br. J. Pharmacol. 103:1053–1056, 1991.

32. Kinoshita S., Kiorpes T. C., Friend J., Thoft R.A. Goblet cell density in ocular surface disease. A better indicator than tear mucin. Arch. Ophthalmol. 101:1284–1287, 1983.

33. Klyce S. D., Crosson C. E. Transport processes across the rabbit corneal epithelium: a review. Curr. Eye Res. 4:323–331, 1985.

34. Kulkarni P. S., Lrinivasan B. D. Cyclooxygenase and lipoxygenase pathways in anterior uvea and conjunctiva. In: The Ocular Effects of Prostaglandins and Other Eicosanoids; edited by Bito L. X. and Stjernshantz J.; Alan R. Liss, Inc.; New York, pp. 39–52, 1989.

35. Kuo K., Rohde J. A. L., Tokuyama K., Barnes P. J., Rogers D. F. Capsaicin and sensory neuropeptide stimulation of goblet cell secretion in guinea-pig trachea. J. Physiol. 431:629–641, 1990.

36. Laburthe M., Augeron C., Rouyer-Fessard C., Roumagnac I., Maoret J., Grasset E., Laboisse C. Functional VIP receptors in the human mucus-secreting colonic epithelial cell line Cl. 16E. Am. J. Physiol. 256:G443–G450, 1989.

37. Lamberts D. W. Physiology of the tear film. In: The Cornea: Scientific Foundations and Clinical Practice; edited by Smolen G. and Thoft R. A.; Little, Brown and Company: Boston, pp. 38–52, 1987.

38. Latkovic S. The ultrastructure of the normal conjunctival epithelium of the guinea pig: III. The bulbar zone, the zone of the fornix and the supranodular zone. Acta Ophthalmol. 57:305–320, 1979.

39. Latkovic S. The ultrastructure of the normal conjunctival epithelium of the guinea pig: IV. The Palpebral and the Perimarginal Zones. Acta Ophthalmol. 57:321–335, 1979.

40. Leikauf G. D., Ueki I. F., Nadel J. A., Widdecombe J. H. Bradykinin stimulates chloride secretion and prostaglandin $E_2$ release by canine tracheal epithelium. Am. J. Physiol. 248:F48–F55, 1985.

41. Lemp M. A. Basic principles and classification of dry eye disorders. In: The Dry Eye: A Comprehensive Guide; edited by Lemp M. A. and Marquardt R.; Springer Verlag: Berlin, pp. 101–132, 1992.

42. Lencer W. I., Reinhart F. D., Neutra M. R. Interaction of cholera toxin with cloned human goblet cells in monolayer culture. Am. J. Physiol. 258:G96–G102, 1990.

43. Luhtala J., Palkama A., Uusitalo H. Calcitonin-gene related peptide immunoreactive nerve fibers in the rat conjunctiva. Invest. Ophthalmol. Vis. Sci. 32:640–645, 1991.

44. Luhtala J., Uusitalo H. The distribution and origin of substance P immunoreactive fibers in the rat conjunctiva. Exp. Eye Res. 53:641–646, 1991.

45. Macintosh S. R. Innervation of the conjunctiva in monkeys: An electron microscopic and nerve degeneration study. Graefes. Arch. Clin. Exp. Ophthalmol. 192:105–116, 1974.

46. McCool D. J., Marcon M. A., Forstner J. F., Forstner G. G. The T84 human colonic adenocarcinoma cell line produces mucin in culture and releases it in response to various secretagogues. Biochem. J. 267:491–500, 1990.

47. Merzel J., LeBlond C. P. Origin and renewal of goblet cells in the epithelium of the mouse small intestine. Am. J. Anat. 124:281–306, 1969.

48. Moore C. P., Wilsman N. J., Nordheim E. V., Majors L. J., Collier L. L. Density and distribution of canine conjunctival goblet cells. Invest. Ophthalmol. Vis. Sci. 28:1925–1932, 1987.

49. Nelson J. D., Wright J. C. Conjunctival goblet cell densities in ocular surface disease. Arch. Ophthalmol. 102:1049–1051, 1984.

50. Neutra M. R., LeBlond C. P. Synthesis of the carbohydrate of mucus in the golgi complex as shown by electron microscope radioautography of goblet cells from rats injected with glucose-$H_3$. J. Cell Biol. 30:119–136, 1966.

51. Neutra M. R., O'Malley L. J., Specian R. D. Regulation of intestinal goblet cell secretion II. A survey of potential secretagogues. Am. J. Physiol. 242:G380–G387, 1982.

52. Norman A. W., Litwach G. Hormones. Academic Press, Inc.: Orlando, pp. 646–647, 1987.

53. Parakal P. F., Matolty A. G. The fine structure of the lipid droplets in the meibomian gland of the mouse. J. Ultrastruct. Res. 10:417–421, 1964.

54. Payne N. A., Gerber J. G. Parietal cell preparation and arachidonate metabolism. Methods Enzymol. 187:505–513, 1990.

55. Phillps T. E. Both crypt and villus intestinal goblet cells secrete mucin in response to cholinergic stimulation. Am. J. Physiol. 262:G327–G331, 1992.

56. Phillips T. E., Phillips T. H., Neutra M. R. Regulation of intestinal goblet cell secretion III. Isolated intestinal eipthelium. Am. J. Physiol. 247:G674–G681, 1984.

57. Phillips T. E., Phillips T. H., Neutra M. R. Regulation of intestinal goblet cell secretion IV. Electrical field stimulation in vitro. Am. J. Physiol. 247:G682–G687, 1984.

58. Piomelli D., Greengard P. Lipoxygenase metabolites of arachidonic acid in neuronal transmembrane signaling. Trends in Pharm. Sci. 11:367–373, 1990.

59. Rieves R. D., Goff J., Wu T., Larivee P., Logan C., Shelhamer J. H. Airway eipthelial cell mucin release: immunologic quantitation and response to platelet-activating factor. Am. J. Respir. Cell. Mol. Biol. 6:158–167, 1992.

60. Roomi N., Labruthe M., Fleming N., Crowther R., Forstner J. Cholera-induced mucin secretion from rat intestine: lack of effect of cAMP, cyclohexamide, VIP, and colchicine. Am. J. Physiol. 247:G140–G148, 1984.

61. Roth S. Cytochemical localization of terminal N-acetyl-Dgalactosamine residues in cellular compartments of intestinal goblet cells; implications for the topology of O-glycosylation. J. Cell Biol. 98:399–406, 1985.

62. Ruskell G. L. Innervation of the conjunctiva. Trans. Ophthalmol. Soc. UK 104:390–395, 1985.

63. Shellans S., Rich L. F., Louiselie I. Conjunctival goblet cell response to vasoconstrictor use. J. Ocular Pharm. 5:217–220, 1989.

64. Smith A. C., Podolsky D. K. Biosynthesis and secretion of human colonic mucin glycoproteins. J. Clin. Invest. 80:300–307, 1987.

65. Smith W. L. The eicosanoids and their biochemical mechanisms of action. Biochem. J. 259:315–324, 1989.

66. Sommer A., Green W. R. Goblet cell response to vitamin A treatment for corneal xerophthalmia. Am. J. Ophthalmol. 94:213–215, 1982.

67. Specian R. D., Neutra M. R. Mechanism of rapid mucus secretion in goblet cells stimulated by acetylcholine. J. Cell Biol. 85:626–640, 1980.

68. Speican R. D., Neutra M. R. Regulation of intestinal goblet cell secretion I. Role of parasympathetic stimulation. Am. J. Physiol. 242:G370–G379, 1982.

69. Specian R. D., Neutra M. R. Cytoskeleton of intestinal goblet cells in rabbit and monkey. The theca. Gastronenterology 87:1313–1325, 1984.

70. Specian R. D., Oliver M. G. Functional biology of intestinal goblet cells. Am. J. Physiol. 260:C183–C193, 1991.

71. Specian R. D., Zhang S. J., Sibley D. A., Kemper A. C., Oliver M. G. Recovery of goblet cells from an accelerated secretory event. Anat. Rec. 226:97A, 1990.

72. Srinivasan B. D., Jakobiec F. A., Iwamoto T. Conjunctiva. In: Ocular Anatomy, Embryology, and Teratology; edited by F. A. Jakobiec. Philadelphia; Harper and Row, pp. 733–760, 1982.

73. Srinivasan B. D., Worgul B. V., Iwamoto T., Merriam G. The conjunctival epithelium. II. Histochemical and ultrastructrual studies on human and rat conjunctiva. Ophthalmic Res. 9:65–79, 1977.

74. Stone R. A., Vasoactive intestinal polypeptide and the ocular innervation. Invest. Ophthalmol. Vis. Sci. 27:951–957, 1986.

75. Stone R. A., Kuwayama Y., Laites A. M. Regulatory peptides in the eye. Experentia 43:791–800, 1987.

76. Tanelian D. L. Cholinergic activation of a population of corneal afferent nerves. Exp. Brain Res. 86:414–420, 1991.

77. Tinsley P. W., Fridland G. H., Killmar J. T., Desiderio D. M. Purification, characterization and localization of neuropeptides in the cornea. Peptides 9:1373–1379, 1989.

78. Tokuyama K., Kuo H. Rohde J. A. L., Barnes P. J., Rogers D. F. Neural control of goblet cell secretion in guinea pig airways. Am. J. Physiol. 259:L108–L115, 1990.

79. Tseng S. C. G., Hirst L. W., Farazdaghi M., Green W. R. Goblet cell density and vascularization during conjunctival transdifferentiation. Invest. Ophthalmol. Vis. Sci. 25:1168–1176, 1984.

80. Unger W. G., Butler J. M., Cole D. F., Bloom S. R., McGregor G. P. Substance P, vasoactive intestinal polypeptide (VIP) and somatostatin levels in ocular tissue of normal and sensorily dennervated rabbit eyes. Exp. Eye Res. 32:797–801, 1981.

81. Verdugo P. Goblet cells secretion and mucogenesis. Rev. Physiol. 52:157–176, 1990.

82. Woodward D. F., Hawley S. B., Williams L. S., Ralston T. R., Protzman G. E., Spada C. S., Nieves A. L. Studies on the ocular phamacology of prostaglandin $D_2$. Invest. Ophthalmol. Vis. Sci. 31:138–146, 1990.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method of treating a patient suffering from excess conjunctival goblet cell mucous secretion associated with a disorder of or injury to an eye, said method comprising the steps of:

identifying a patient suffering from excess conjunctival goblet cell mucous secretion associated with a disorder of or injury to an eye;

providing a therapeutic composition comprising a neural system inhibitor selected from the group consisting of adrenergics, cholinergics, dopaminergics, serotonergics, neuropeptides, neurotoxins, ion channel modulators and local anesthetics, in a pharmaceutically acceptable carrier substance; and administering to an affected eye of said patient a therapeutically effective amount of said composition.

2. The method of claim 1, wherein said patient is a human patient.

3. The method of claim 1, wherein in said administering step, said therapeutic composition is applied topically to an ocular surface.

4. The method of claim 1, wherein in said administering step, said therapeutic composition is applied subcutaneously to a region of to an eye of said patient adjacent an ocular surface.

5. The method of claim 1, wherein said therapeutic composition comprises a neural system inhibitor selected from the group consisting of lidocaine, atropine, prazosin, phentolamine, timolol, haloperidol, methysergide, [4-Cl-D-Phe$^6$, Leu$^{17}$]-Vasoactive Intestinal Peptide and [D-Arg$^1$, D-Phe$^5$,D-Tryp$^{7,9}$, Leu$^{11}$]-Substance P.

6. An article of manufacture comprising packaging material and a therapeutic composition contained within said packaging material, wherein the therapeutic composition is therapeutically effective for controlling excess conjunctival goblet cell mucous secretion, and wherein the packaging material comprises a label that indicates that the therapeutic composition can be used for controlling excess conjunctival goblet cell mucous secretion associated with a disorder of or injury to an eye, and wherein said therapeutic composition comprises a neural system inhibitor selected from the group consisting of adrenergics, cholinergics, dopaminergics, serotonergics, neuropeptides, neurotoxins, ion channel modulators and local anesthetics, in a pharmaceutically acceptable carrier substance.

7. The article of manufacture of claim 6, wherein said therapeutic composition comprises a neural system inhibitor selected from the group consisting of lidocaine, atropine, prazosin, phentolamine, timolol, haloperidol, methysergide, [4-Cl-D-Phe$^6$, Leu$^{17}$]-Vasoactive Intestinal Peptide and [D-Arg$^1$, D-Phe$^5$,D-Tryp$^{7,9}$, Leu$^{11}$]-Substance P.

* * * * *

UNITED STATES PATENT AND TRADEMARK OFFICE
CERTIFICATE OF CORRECTION

PATENT NO.    : 5,545,617
DATED         : August 13, 1996
INVENTOR(S)   : Darlene A. Dartt et al.

Page 1 of 1

It is certified that error appears in the above-identified patent and that said Letters Patent is hereby corrected as shown below:

<u>Column 1,</u>
Line 9, insert the following sentence -- The supporting grant number for this is NIH-EY09057. --.

Signed and Sealed this

Twentieth Day of July, 2004

JON W. DUDAS
*Acting Director of the United States Patent and Trademark Office*